US007825227B2

(12) United States Patent
Boniface et al.

(10) Patent No.: US 7,825,227 B2
(45) Date of Patent: Nov. 2, 2010

(54) METHOD FOR PURIFICATION OF A PROTEIN COMPLEX AND IDENTIFICATION OF ITS COMPONENTS

(75) Inventors: John J. Boniface, Salt Lake City, UT (US); Vladimir Kery, Richland, WA (US); John M. Peltier, Sandy, UT (US); Paul B. Robbins, Park City, UT (US); Justin Savage, North Salt Lake, UT (US); Moritz Von Rechenberg, Salt Lake City, UT (US)

(73) Assignee: Prolexys Pharmaceuticals, Inc., Salt Lake City, UT (US)

( * ) Notice: Subject to any disclaimer, the term of this patent is extended or adjusted under 35 U.S.C. 154(b) by 0 days.

(21) Appl. No.: 10/984,958

(22) Filed: Nov. 9, 2004

(65) Prior Publication Data

US 2005/0118646 A1    Jun. 2, 2005

Related U.S. Application Data

(63) Continuation-in-part of application No. PCT/US03/14511, filed on May 9, 2003.

(60) Provisional application No. 60/519,148, filed on Nov. 12, 2003, provisional application No. 60/379,317, filed on May 9, 2002.

(51) Int. Cl.
 *A23J 1/00*   (2006.01)
 *C12P 21/04*   (2006.01)
(52) U.S. Cl. ...................... 530/412; 435/69.7
(58) Field of Classification Search ............... 530/412; 435/69.7
See application file for complete search history.

(56) References Cited

U.S. PATENT DOCUMENTS 5,732,584 A * 3/1998 Prater et al. ................... 72/187
5,874,239 A * 2/1999 Schatz ....................... 435/69.1
5,932,433 A * 8/1999 Schatz ........................... 435/15
2002/0061513 A1* 5/2002 Seraphin et al. ................. 435/4
2004/0265902 A1* 12/2004 Fricker et al. ................. 435/7.1

OTHER PUBLICATIONS

Mayer et al., "Isolation of viral ribonucleoprotein complexes from infected cells by tandem affinity purification," Proteomics 2005, 5, 4483-4487.*
Uhien et al. Methods in Enzymology, 1990, vol. 185, pp. 129-143.*
Honey et al. Nucleic Acids Residue. 2001, vol. 29, No. 4, pp. 1-9.*
Nilsson et al. Jouranl of Molecular Recognition, 1996, vol. 9, pp. 585-594.*
Avidity Product p. For AviTag, pp. 1-4. No date.*
Cai et al. Analytical Biochemistry, 2001, 290: 186-204.*
Cull & Schatz, Methods in Enzymology, 2000, 326:430-440.*

* cited by examiner

*Primary Examiner*—Suzanne M. Noakes
(74) *Attorney, Agent, or Firm*—Greenlee Sullivan P.C.

(57) ABSTRACT

The present invention provides a method for purifying a protein complex and the components comprising the complex from a cell, a cell or tissue lysate or a whole organism by employing a combined set of affinity tags of high affinity, specificity and ease of elution. The method involves using a protein or a peptide modified to contain one or more affinity tags separated by one or more specific protease cleavage sites to isolate any interacting proteins or fragments thereof. Specifically exemplified is a method employing a modified bait containing AviTag or GST and a removal tag of $His_6$ hexapeptide positioned proximal to the bait such that any excess bait can be efficiently removed from the purified complex yielding enriched interacting proteins prior to subjecting the complex for further identification of individual components. The identification of the proteins or fragments thereof contained in the protein complex will provide new targets for the identification of new pharmaceuticals and diagnostic tools.

14 Claims, 9 Drawing Sheets

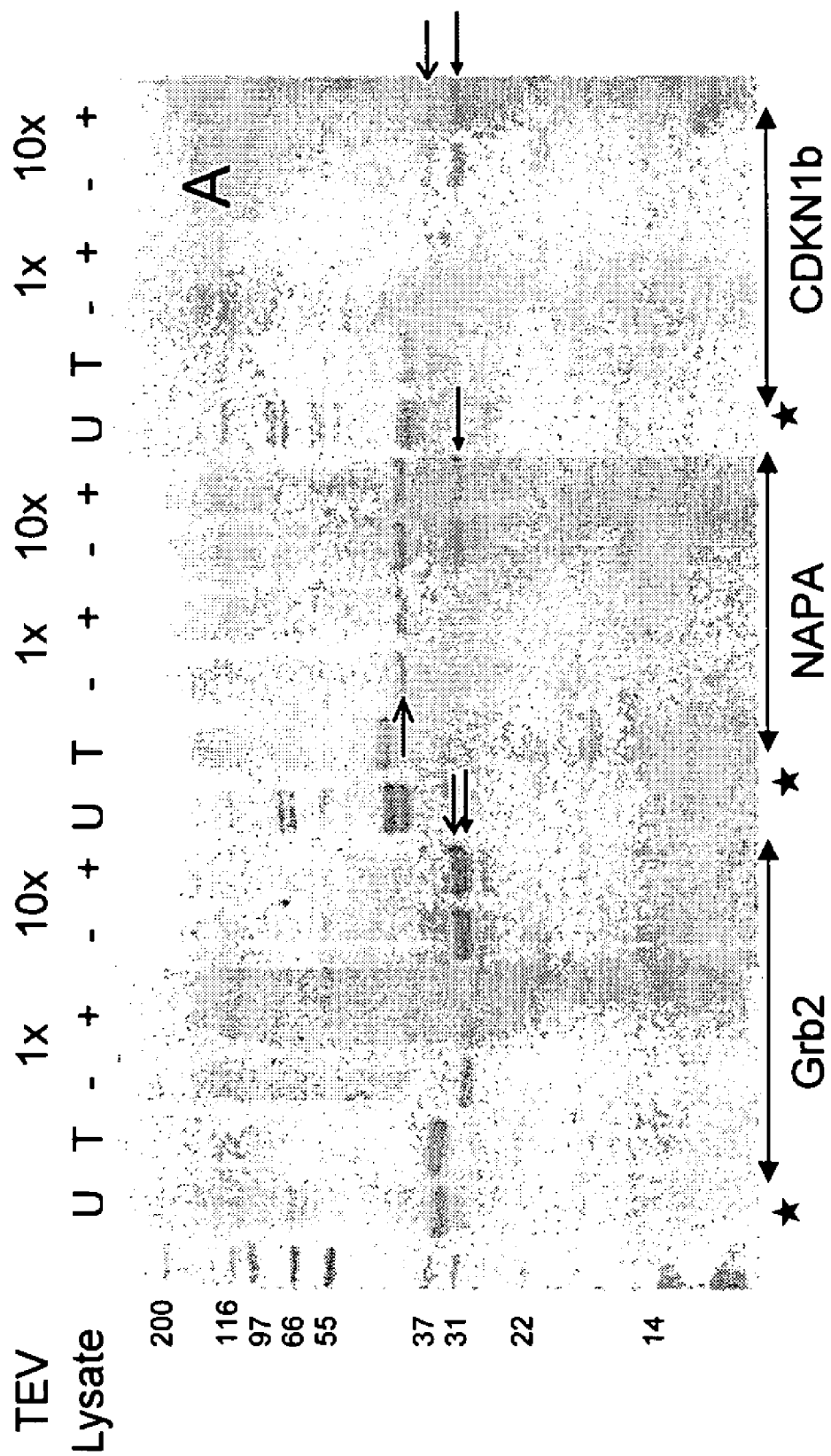

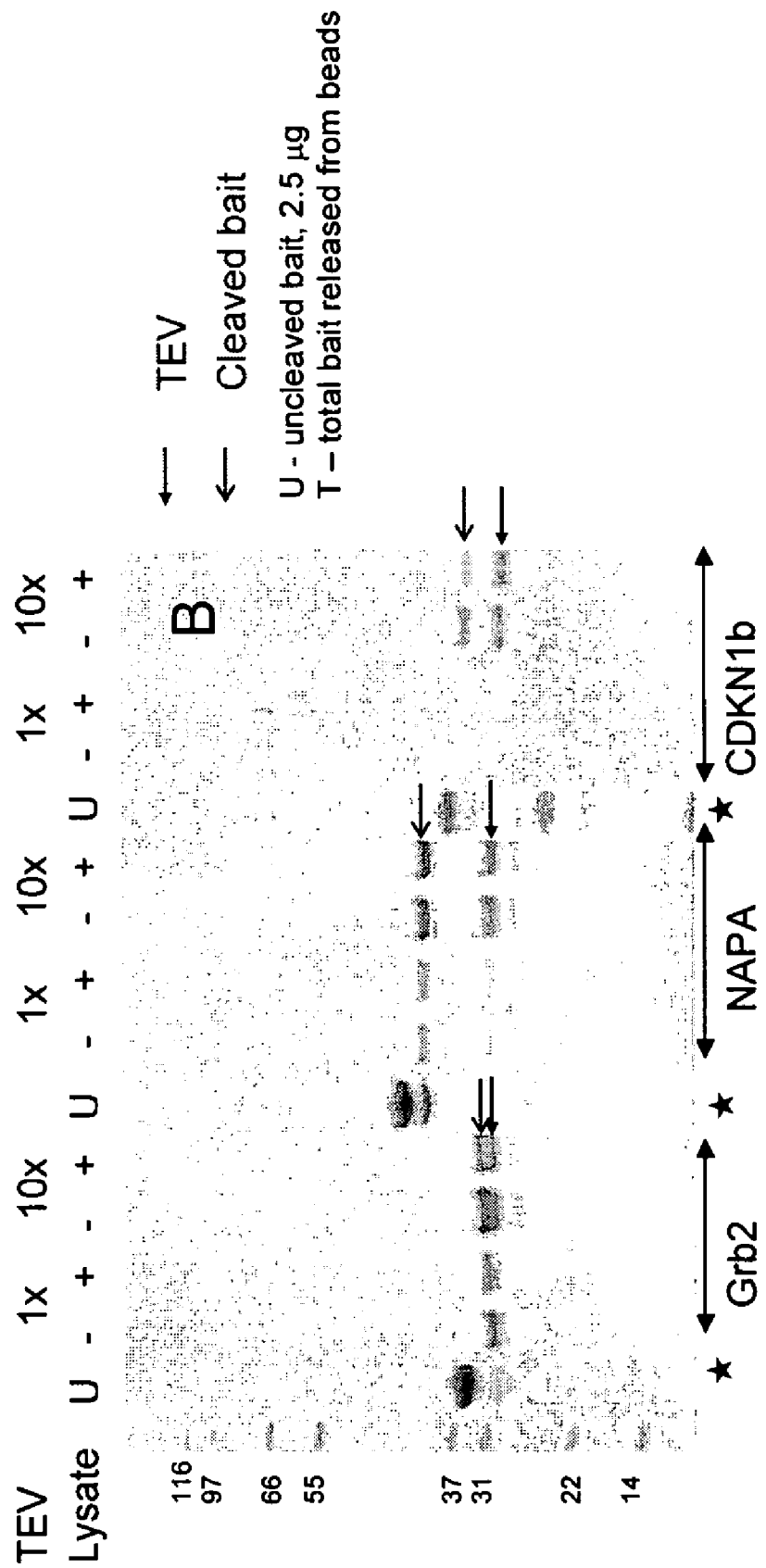

SEQUENCE LISTING

<160> NUMBER OF SEQ ID NOS: 36

<210> SEQ ID NO 1
<211> LENGTH: 4
<212> TYPE: PRT
<213> ORGANISM: Artificial sequence
<220> FEATURE:
<223> OTHER INFORMATION: Synthetic peptide of FLAG M1 antibody
      recognition sequence

<400> SEQUENCE: 1

Asp Tyr Lys Asp
1

<210> SEQ ID NO 2
<211> LENGTH: 5
<212> TYPE: PRT
<213> ORGANISM: Artificial sequence
<220> FEATURE:
<223> OTHER INFORMATION: Synthetic peptide of FLAG M1 antibody
      recognition sequence

<400> SEQUENCE: 2

Asp Tyr Lys Asp Glu

-continued

```
<210> SEQ ID NO 3
<211> LENGTH: 7
<212> TYPE: PRT
<213> ORGANISM: Artificial sequence
<220> FEATURE:
<223> OTHER INFORMATION: Synthetic peptide of FLAG M1 antibody
      recognition sequence

<400> SEQUENCE: 3

Asp Tyr Lys Asp Asp Asp Asp
1               5

<210> SEQ ID NO 4
<211> LENGTH: 4
<212> TYPE: PRT
<213> ORGANISM: Artificial sequence
<220> FEATURE:
<223> OTHER INFORMATION: Synthetic peptide of Factor Xa protease
      recognition sequence
<220> FEATURE:
<221> NAME/KEY: MISC_FEATURE
<222> LOCATION: (2)..(2)
<223> OTHER INFORMATION: X is Asp or Glu.

<400> SEQUENCE: 4

Ile Xaa Gly Arg
1

<210> SEQ ID NO 5
<211> LENGTH: 12
<212> TYPE: PRT
<213> ORGANISM: Artificial sequence
<220> FEATURE:
<223> OTHER INFORMATION: Synthetic peptide of Protein C tag

<400> SEQUENCE: 5

Glu Asp Gln Val Asp Pro Arg Leu Ile Asp Gly Lys
1               5                   10

<210> SEQ ID NO 6
<211> LENGTH: 17
<212> TYPE: PRT
<213> ORGANISM: Artificial sequence
<220> FEATURE:
<223> OTHER INFORMATION: Synthetic peptide of E. coli biotin ligase
      gene, specifically of the BirA recognition sequence

<400> SEQUENCE: 6

Met Ser Gly Leu Asn Asp Ile Phe Glu Ala Gln Lys Ile Glu Trp His
1               5                   10                  15

Glu

<210> SEQ ID NO 7
<211> LENGTH: 7
<212> TYPE: PRT
<213> ORGANISM: Artificial sequence
<220> FEATURE:
<223> OTHER INFORMATION: Synthetic peptide of TEV protease
      recognition sequence

<400> SEQUENCE: 7

Glu Asn Leu Tyr Phe Gln Gly
1               5

<210> SEQ ID NO 8
```

```
<211> LENGTH: 6
<212> TYPE: PRT
<213> ORGANISM: Artificial sequence
<220> FEATURE:
<223> OTHER INFORMATION: Synthetic peptide of hexahistidine, a
      peptide capable of binding metal, e.g. nickel

<400> SEQUENCE: 8

His His His His His His
1               5

<210> SEQ ID NO 9
<211> LENGTH: 8
<212> TYPE: PRT
<213> ORGANISM: Artificial sequence
<220> FEATURE:
<223> OTHER INFORMATION: Synthetic peptide of protease PreScission
      recognition sequence

<400> SEQUENCE: 9

Leu Glu Val Leu Phe Gln Gly Pro
1               5

<210> SEQ ID NO 10
<211> LENGTH: 26
<212> TYPE: PRT
<213> ORGANISM: Artificial sequence
<220> FEATURE:
<223> OTHER INFORMATION: Synthetic peptide of Calmodulin binding domain

<400> SEQUENCE: 10

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 11
<211> LENGTH: 4
<212> TYPE: PRT
<213> ORGANISM: Artificial sequence
<220> FEATURE:
<223> OTHER INFORMATION: Synthetic peptide of Furin recognition sequence
<220> FEATURE:
<221> NAME/KEY: MISC_FEATURE
<222> LOCATION: (2)..(2)
<223> OTHER INFORMATION: X is any amino acid.
<220> FEATURE:
<221> NAME/KEY: MISC_FEATURE
<222> LOCATION: (3)..(3)
<223> OTHER INFORMATION: X is Lys or Arg.

<400> SEQUENCE: 11

Arg Xaa Xaa Arg
1

<210> SEQ ID NO 12
<211> LENGTH: 11
<212> TYPE: PRT
<213> ORGANISM: Artificial sequence
<220> FEATURE:
<223> OTHER INFORMATION: Sythetic peptide of Myc tag

<400> SEQUENCE: 12

Glu Gln Leu Lys Leu Ile Ser Glu Glu Asp Leu
1               5                   10

<210> SEQ ID NO 13
<211> LENGTH: 9
```

-continued

<212> TYPE: PRT
<213> ORGANISM: Artificial sequence
<220> FEATURE:
<223> OTHER INFORMATION: Synthetic peptide of Hemagglutinin sequence

<400> SEQUENCE: 13

Tyr Pro Tyr Asp Val Pro Asp Tyr Ala
1               5

<210> SEQ ID NO 14
<211> LENGTH: 6
<212> TYPE: PRT
<213> ORGANISM: Artificial sequence
<220> FEATURE:
<223> OTHER INFORMATION: Synthetic peptide of Thrombin
      recognition sequence

<400> SEQUENCE: 14

Leu Val Pro Arg Gly Ser
1               5

<210> SEQ ID NO 15
<211> LENGTH: 5
<212> TYPE: PRT
<213> ORGANISM: Artificial sequence
<220> FEATURE:
<223> OTHER INFORMATION: Synthetic peptide of Enterokinase
      recognition sequence

<400> SEQUENCE: 15

Asp Asp Asp Asp Lys
1               5

<210> SEQ ID NO 16
<211> LENGTH: 47
<212> TYPE: DNA
<213> ORGANISM: Artificial sequence
<220> FEATURE:
<223> OTHER INFORMATION: Synthetic nucleotide primer

<400> SEQUENCE: 16
ggaaccggtg aaggagatag aaccatgtcc cctatactag gttattg 47

<210> SEQ ID NO 17
<211> LENGTH: 31
<212> TYPE: DNA
<213> ORGANISM: Artificial sequence
<220> FEATURE:
<223> OTHER INFORMATION: Synthetic nucleotide primer

<400> SEQUENCE: 17
tccctcgagc ctggtaccga aagtgccccg g 31

<210> SEQ ID NO 18
<211> LENGTH: 80
<212> TYPE: DNA
<213> ORGANISM: Artificial sequence
<220> FEATURE:
<223> OTHER INFORMATION: Synthetic nucleotide primer

<400> SEQUENCE: 18
ccgaattccc tggaagttct gttccaggga cctcatcacc atcaccatca cggtggtggc 60
ggttccctcg agcgatcgat 80

<210> SEQ ID NO 19
<211> LENGTH: 20

<212> TYPE: PRT
<213> ORGANISM: Artificial sequence
<220> FEATURE:
<223> OTHER INFORMATION: Synthetic peptide of Junction sequence
      in E04 vector

<400> SEQUENCE: 19

Pro Asn Leu Ser Glu Val Leu Phe Gln Gly Pro His His His His
1               5                   10                  15

His Gly Gly Gly
            20

<210> SEQ ID NO 20
<211> LENGTH: 248
<212> TYPE: PRT
<213> ORGANISM: Artificial sequence
<220> FEATURE:
<223> OTHER INFORMATION: Artificial peptide of E23 tag region

<400> SEQUENCE: 20

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Ser Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser Pro Asn Ser Leu Glu Val Leu Phe Gln Gly Pro His His His
225                 230                 235                 240

His His His Gly Gly Gly Gly Ser
                245

<210> SEQ ID NO 21
<211> LENGTH: 744
<212> TYPE: DNA
<213> ORGANISM: Artificial sequence
<220> FEATURE:
<223> OTHER INFORMATION: Artificial DNA encoding E23 tag sequence -continued

<400> SEQUENCE: 21

```
atgtccccta tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg agtttcccaa tcttccttat tatatattgat    180
ggtgatgtta aattaacaca gtctatggcc atcatacgtt atatagctga caagcacaac     240
atgttgggtg ttgtccaaa agagcgtgca gagatttcaa tgcttgaagg agcggttttg      300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600
tggcctttgc agggctggca agccacgttt ggtggtggcg accatcctcc aaaatcggat    660
ctggttccgc gtggatcccc gaattccctg aagttctgt ccagggacc tcatcaccat     720
caccatcacg gtggtggcgg ttcc                                           744
```

<210> SEQ ID NO 22
<211> LENGTH: 52
<212> TYPE: PRT
<213> ORGANISM: Artificial sequence
<220> FEATURE:
<223> OTHER INFORMATION: Artificial peptide of E24 tag

<400> SEQUENCE: 22

```
Met Ser Gly Leu Asn Asp Ile Phe Glu Ala Gln Lys Ile Glu Trp His
1               5                   10                  15
Glu Gly Ala Ile Ser Ala Glu Asn Leu Tyr Phe Gln Gly Ser Ser Ala
            20                  25                  30
His His His His His His Gly Ser Glu Ser Gln Val Asp Pro Arg Leu
        35                  40                  45
Ile Asp Gly Lys
    50
```

<210> SEQ ID NO 23
<211> LENGTH: 156
<212> TYPE: DNA
<213> ORGANISM: Artificial sequence
<220> FEATURE:
<223> OTHER INFORMATION: Artificial DNA encoding E24 tag

<400> SEQUENCE: 23

```
atgtccggcc tgaacgacat cttcgaggct cagaaaatcg aatggcacga aggcgcgata     60
tccgcggaga acctgtactt ccagggcagc agcgctcatc accatcacca tcacgggagc    120
gaagatcagg tagatccacg gttaatcgat ggtaag                              156
```

<210> SEQ ID NO 24
<211> LENGTH: 67
<212> TYPE: PRT
<213> ORGANISM: Artificial sequence
<220> FEATURE:
<223> OTHER INFORMATION: Artificial peptide of E25 tag

<400> SEQUENCE: 24

```
Met Ser Gly Leu Asn Asp Ile Phe Glu Ala Gln Lys Ile Glu Trp His
1               5                   10                  15
```

-continued

```
Glu Gly Ala Ile Ser Gly Gly Gly Ser Gly Gly Gly Ser Gly
            20                  25                  30

Gly Gly Gly Ser Ala Glu Asn Leu Tyr Phe Gln Gly Ser Ser Ala His
        35                  40                  45

His His His His His Gly Ser Glu Asp Gln Val Asp Pro Arg Leu Ile
    50                  55                  60

Asp Gly Lys
65

<210> SEQ ID NO 25
<211> LENGTH: 201
<212> TYPE: DNA
<213> ORGANISM: Artificial sequence
<220> FEATURE:
<223> OTHER INFORMATION: Artificial DNA encoding E25 tag

<400> SEQUENCE: 25
atgtccggcc tgaacgacat cttcgaggct cagaaaatcg aatggcacga aggcgcgata      60
tccggcggcg gcggcagcgg cggcggcggc agcggcggcg gcggcagcgc ggagaacctg     120
tacttccagg gcagcagcgc tcatcaccat caccatcacg ggagcgaaga tcaggtagat     180
ccacggttaa tcgatggtaa g                                               201

<210> SEQ ID NO 26
<211> LENGTH: 54
<212> TYPE: PRT
<213> ORGANISM: Artificial sequence
<220> FEATURE:
<223> OTHER INFORMATION: Artificial peptide of M07 tag
<220> FEATURE:
<221> NAME/KEY: MISC_FEATURE
<222> LOCATION: (48)..(54)
<223> OTHER INFORMATION: X is any amino acid.

<400> SEQUENCE: 26

Met Ser Gly Leu Asn Asp Ile Phe Glu Ala Gln Lys Ile Glu Trp His
1               5                   10                  15

Glu Gly Ala Ile Ser Ala Glu Asn Leu Tyr Phe Gln Gly Ser Ser Ala
            20                  25                  30

His His His His His His Val Leu Glu Val Leu Phe Gln Gly Pro Xaa
        35                  40                  45

Xaa Xaa Xaa Xaa Xaa Xaa
    50

<210> SEQ ID NO 27
<211> LENGTH: 148
<212> TYPE: DNA
<213> ORGANISM: Artificial sequence
<220> FEATURE:
<223> OTHER INFORMATION: Artificial DNA encoding M07 tag
<220> FEATURE:
<221> NAME/KEY: misc_feature
<222> LOCATION: (142)..(148)
<223> OTHER INFORMATION: N is A, T, G or C.

<400> SEQUENCE: 27
atgtccggcc tgaacgacat cttcgaggct cagaaaatcg aatggcacga aggcgcgata      60
tccgcggaga acctgtactt ccagggcagc agcgctcatc accatcacca tcacgtgctg     120
gaagttctgt tccaggggcc cnnnnnnn                                        148

<210> SEQ ID NO 28
```

<211> LENGTH: 62
<212> TYPE: PRT
<213> ORGANISM: Artificial sequence
<220> FEATURE:
<223> OTHER INFORMATION: Artificial peptide of M08 tag

<400> SEQUENCE: 28

Met Ser Gly Leu Asn Asp Ile Phe Glu Ala Gln Lys Ile Glu Trp His
1               5                   10                  15

Glu Gly Ala Ile Ser Gly Gly Gly Ser Gly Gly Gly Gly Ser Gly
            20                  25                  30

Gly Gly Gly Ser Ala Glu Asn Leu Tyr Phe Gln Gly Ser Ser Ala His
        35                  40                  45

His His His His His Val Leu Glu Val Leu Phe Gln Gly Pro
    50                  55                  60

<210> SEQ ID NO 29
<211> LENGTH: 186
<212> TYPE: DNA
<213> ORGANISM: Artificial sequence
<220> FEATURE:
<223> OTHER INFORMATION: Artificial DNA encoding M08 tag

<400> SEQUENCE: 29
atgtccggcc tgaacgacat cttcgaggct cagaaaatcg aatggcacga aggcgcgata      60
tccggcggcg gcggcagcgg cggcggcggc agcggcggcg gcggcagcgc ggagaacctg     120
tacttccagg gcagcagcgc tcatcaccat caccatcacg tgctggaagt tctgttccag     180
gggccc                                                                186

<210> SEQ ID NO 30
<211> LENGTH: 52
<212> TYPE: PRT
<213> ORGANISM: Artificial sequence
<220> FEATURE:
<223> OTHER INFORMATION: Artificial peptide of M09 tag

<400> SEQUENCE: 30

Met Ser Gly Leu Asn Asp Ile Phe Glu Ala Gln Lys Ile Glu Trp His
1               5                   10                  15

Glu Gly Ala Ile Ser Ala Glu Asn Leu Tyr Phe Gln Gly Ser Ser Ala
            20                  25                  30

His His His His His His Gly Ser Glu Asp Gln Val Asp Pro Arg Leu
        35                  40                  45

Ile Asp Gly Lys
    50

<210> SEQ ID NO 31
<211> LENGTH: 156
<212> TYPE: DNA
<213> ORGANISM: Artificial sequence
<220> FEATURE:
<223> OTHER INFORMATION: Artificial DNA encoding M09 tag

<400> SEQUENCE: 31
atgtccggcc tgaacgacat cttcgaggct cagaaaatcg aatggcacga aggcgcgata      60
tccgcgagca gcgctcatca ccatcaccat cacgagaacc tgtacttcca gggcgggagc     120
gaagatcagg tagatccacg gttaatcgat ggtaag                               156

<210> SEQ ID NO 32
<211> LENGTH: 5

```
<212> TYPE: PRT
<213> ORGANISM: Artificial sequence
<220> FEATURE:
<223> OTHER INFORMATION: Artificial peptide of spacer sequence

<400> SEQUENCE: 32

Gly Gly Gly Gly Ser
1               5

<210> SEQ ID NO 33
<211> LENGTH: 42
<212> TYPE: DNA
<213> ORGANISM: Artificial sequence
<220> FEATURE:
<223> OTHER INFORMATION: Synthetic nucleotide primer

<400> SEQUENCE: 33
ggaaccggtg aaggagatag aaccatgtcc ggcctgaacg ac                    42

<210> SEQ ID NO 34
<211> LENGTH: 32
<212> TYPE: DNA
<213> ORGANISM: Artificial sequence
<220> FEATURE:
<223> OTHER INFORMATION: Synthetic nucleotide primer

<400> SEQUENCE: 34
tccctcgagc cgtcgtcgtc atccttgtag tc                               32

<210> SEQ ID NO 35
<211> LENGTH: 42
<212> TYPE: DNA
<213> ORGANISM: Artificial sequence
<220> FEATURE:
<223> OTHER INFORMATION: Synthetic nucleotide primer

<400> SEQUENCE: 35
gacgagctcg tttagtgaac cgtcagatcg cctggagacg cc                    42

<210> SEQ ID NO 36
<211> LENGTH: 96
<212> TYPE: DNA
<213> ORGANISM: Artificial sequence
<220> FEATURE:
<223> OTHER INFORMATION: Synthetic nucleotide primer

<400> SEQUENCE: 36
catgacgagc tagctagcct cgagcttacc atcgattaac cgtggatcta cctgatcttc    60
gctcccgtga tggtgatggt gatgagcgct gctgcc                              96
```

METHOD FOR PURIFICATION OF A PROTEIN COMPLEX AND IDENTIFICATION OF ITS COMPONENTS

CROSS REFERENCE TO RELATED APPLICATIONS

The present application is a Continuation-In-Part Application of International Application PCT/US03/14511 filed May 9, 2003, which claims priority from U.S. Provisional Application Ser. No. 60/379,317 filed May 9, 2002. This application also claims priority from U.S. Provisional Application Ser. No. 60/519,148 filed Nov. 12, 2003, all of which are incorporated by reference to the extent not inconsistent herewith.

BACKGROUND OF THE INVENTION

The present invention relates to efficient methods for purifying a protein complex and its individual components comprising the complex from a cell, a cell lysate or tissue lysate or an organism.

In living cells, complex processes are typically accomplished by highly specific binding interactions among functional cell components, most commonly involving one or more proteins. Understanding which proteins bind to one another, and under what circumstances, poses difficult unsolved problems. An approach to learning which proteins bind to each other to form protein complexes is to isolate functional protein complexes, or portions thereof, in order to identify their components.

Recent advances in human genomics research have led to rapid progress in the identification of novel genes. In biological and pharmaceutical research, there is a need to determine the functions of gene products. An important step in defining the function of a novel gene is to determine its interactions with other gene products in the appropriate context. Several approaches have been devised towards this goal of determining a novel gene product's physical interaction with other gene products.

Specifically, yeast two-hybrid systems have been extensively employed to define interactions existing among proteins. The principles and methods of the yeast two-hybrid system have been described in detail elsewhere [Bartel and Fields (1997) The Yeast Two-Hybrid System, Oxford University Press, New York; Fields and Song (1989) *Nature* 340: 245-246]. However, the number of false-positives and false-negatives arising from yeast two hybrid screening is high and thus extensive experimentation is required to validate the interactions observed in this system. Moreover, a yeast two hybrid experiment results in the identification of a pair of directly interacting proteins. For this reason, yeast-two hybrid is not directly useful for identifying higher order structures in multiprotein complexes comprised of both direct and indirect protein associations.

There is a continuing need for the discovery of additional protein-protein interactions that are physiologically relevant. The present invention provides an efficient method for purifying protein complexes from a cell, cell lysate, tissue lysate or organism by employing a combined set of affinity tags attached to a known protein as bait. The invention further provides an efficient method for purifying individual components comprising the complex from the excess bait used in the protein complex purification process. The interacting proteins purified according to the invention are identified by employing various art-known methods including mass spectrometric analyses. The advantages of the invention will be evident in the following description.

SUMMARY OF THE INVENTION

The present invention provides efficient methods for purifying a protein complex and individual components comprising the complex from a cell, a cell or tissue lysate or an organism by employing a combined set of affinity tags of high affinity, specificity and ease of elution. The method typically involves using a known protein, termed "bait", modified to contain one or more affinity tags which may be separated by one or more specific protease cleavage sites to isolate any interacting proteins or fragments thereof. One aspect of the invention has a unique feature of using an affinity tag, termed herein as "removal tag", which is positioned proximal to the bait such that any excess bait can be efficiently removed from the purified protein complex yielding enriched purified components for further identification. This feature is useful for mass spectrometric (MS) analyses of the individual components of the protein complexes, which can be carried out in a high throughput format. The step of the excess bait removal is particularly useful where the individual interacting components present in a given protein complex exist at a low stoichiometric molar ratio with respect to the bait brought about by low overall affinity, transient dissociation kinetics, and/or low starting levels in the source of the complex components.

The general design of the modified bait is [AT1]-[PS1]-[+/−AT2]-[BAIT] or [AT1]-[PS1]-[RT]-[BAIT] if AT2 functions as removal tag. AT1 is affinity tag 1 or first affinity tag, PS1 is protease cleavage sequence 1, AT2 is affinity tag 2 or second affinity tag, and RT is removal tag. The modified portion of a given bait protein can vary depending on the number of affinity tags and protease cleavage sequences. The affinity tags including the removal tag, the protease cleavage sites, the removal tag and the bait can also be separated by a spacer (e.g., short peptide) to vary flexibility and/or spatial separation in the modified bait. The removal tag can also serve as a second affinity purification tag. In all cases it will be understood that a person ordinarily skilled in the art can add and optimize spacer amino acid sequences between any of the contiguous functional segments or between the bait protein and the peptide tail to allow efficient formation of multiprotein complexes, affinity purification and protease digestion.

The modified bait protein is termed herein as a "first binding component". The modified portion of the bait protein can be present as an extension either at the amino terminus or the carboxyl terminus of the bait or at both termini. Alternatively, one or more affinity tags can be inserted in the open-reading frame (ORF) of the bait. The affinity tags in the first binding component serve as a specific means for purifying a desired protein complex bound to the first binding component before and after a protease digestion. The inclusion of the protease specific segment between the affinity tags can provide an enhanced specificity of the second affinity purification step since the protease cleavage can generate a tag sequence that is more selective for the second affinity ligand in certain instances. The design of the second affinity tag segment of the first binding component can be such that two or more tags are assembled in tandem, possibly separated by specific protease sites, different from that between the first affinity recognition sequence and the second affinity tag segment. The removal tag is an affinity tag that functions for bait removal under several possible scenarios. In one instance the removal tag and associated bait are retained by the first affinity matrix, which enables the interacting proteins contained in the complex to be separated therefrom under denaturing conditions. In another example, the removal tag is retained in the second binding component after specific protease cleavage of the first binding component or specific elution. The removal of the bait can then occur under denaturing conditions, in which only the bait and not the interactors are retained on the second affinity matrix by means of the removal tag. Alternatively, the second binding component and the associated complexes are bound to the second affinity matrix via the removal tag and the individual components are eluted under denaturing conditions, while all or a significant amount of the bait protein is retained on said affinity matrix. In principle, any affinity tag can be used as the removal tag. A preferred removal tag is a polyhistidine peptide such as the hexapeptide $His_6$ which is known to bind to a column of nickel ($Ni^{2+}$) or cobalt ($Co^{2+}$) with high affinity. In certain cases, the removal tag can also serve as one of the affinity tags to purify a protein complex.

The use of the removal tag in the invention solves a problem arising from the presence of the excess bait in the purified protein complex. In most methods currently available for purifying a protein complex, excess exogenous bait (typically 1 or 2 orders of magnitude) is used to bias the kinetics in favor of formation or reformation of protein complexes with the exogenously added bait. This in turn may result in a large excess of the bait protein being present following isolation of the protein complex components. The present invention utilizes the removal tag to enrich the interacting proteins comprising the protein complex by separating the excess bait after a desired protein complex is purified. This reduction of the bait can facilitate the identification of said components by MS analysis.

An example of the first binding component is a bait protein containing a biotinylation recognition sequence (e.g. AVI-TAG™, Avidity, Denver, Colo.) that can serve as affinity tag 1(AT1) upon biotinylation and/or a hexapeptide comprised of six histidines ($His_6$) as removal tag (RT) separated by a protease cleavage sequence, e.g., the recognition sequence for TEV (Tobacco Etch Virus) protease. It is possible that the same affinity tag can be used as AT1 as well as RT. Any protein or associated protein complex containing the biotinylated AVITAG™ can be readily purified using a matrix with high affinity for biotin, such as avidin, streptavidin, NEU-TRAVIDIN™ or TETRALINK™ (Promega, Miadison, Wis.).

Another example of the first binding component is a bait protein containing an amino acid sequence encoding Glutathione-S-Transferase (GST) as AT1 and a hexapeptide $His_6$ as the RT, separated by a protease cleavage sequence (e.g. PRESCISSION™). Any protein containing the GST sequence can be readily purified using a matrix (e.g., beads) containing a GST ligand, for example, glutathione.

Provided herein is a method for purifying a protein complex and interacting protein(s) comprising a complex from a cell, a cell or tissue lysate, or an organism, comprising the steps of: a) providing a first binding component comprised of four parts: 1) first affinity tag, 2) a protease specificity segment, 3) second affinity tag, and 4) a bait; b) contacting the first binding component with proteins or a protein complex, whereby part 4) of the first binding component binds to said proteins or protein complex, forming a bait-bound protein complex; c) contacting the bait-bound complex formed in step b) with a first affinity matrix specific for the first affinity tag thereby binding said bait-bound complex to said matrix, and separating the bait-bound complex from unbound material; and d) further separating the individual components of the complex from the first binding component bound to the matrix, whereby purified individual components are obtained.

The steps of the method of the invention will vary depending on the number and the type of the affinity tags including the removal tag and the protease specificity segments. Accordingly, the method can be practiced with various modifications. For example, the affinity matrix-bound protein complex formed in step c) can be further, i) contacted with a protease that specifically cleaves part 2) of the first binding component thereby generating a second binding component comprising the second affinity tag or removal tag and the bait bound to the protein complex; ii) the affinity or removal tag of the second binding component is contacted with a second affinity matrix specific for the second affinity or removal tag thereby binding the protein complex to the second affinity matrix and separating further the bait-bound protein complex from unbound material; iii) the individual components comprising the complex are separated from the bait-bound protein complex attached to the second matrix, whereby purified individual components are obtained. Alternatively, the method of the invention can also be practiced in the following manner; after step c) of the method described above, the affinity matrix-bound protein complex formed in step c) can be detached from the first affinity matrix and the detached complex is contacted with a second affinity matrix specific for the second affinity or removal tag, thereby binding said complex to said matrix, and separating the complex from unbound material. The individual components of the complex from the first binding component bound to the second matrix can be separated to yield purified individual components. Yet another embodiment of the invention include a method with the following variation; after step c) of the method described above, the protein complex formed in step c) can be detached from the first affinity matrix as a mixture of the complex and individual components, which in turn are contacted with a second affinity matrix specific for the second affinity tag where the second affinity tag (or removal tag) binds to the second affinity matrix and separating the individual components from the excess bait (or first binding component) in the mixture.

It will be understood to those of ordinary skill in the art that the method of the invention can be practiced with certain variations including reversing the order of the steps, omitting a particular step(s) or a combination thereof. For example, the first binding component can first be bound to an affinity matrix specific for the affinity tag prior to being subjected to the step b) of the method. In this scenario, the step c) will be modified accordingly, i.e., the bait-bound complex formed in step b) is already attached to the affinity matrix. It is also possible to practice the invention with or without a specific protease digestion step. Additionally, when the first binding component contains AVITAG™, a protein complex can be purified and the release of individual components can be achieved in a single affinity step of subjecting the bait bound protein complex to a matrix containing strepavidin, and eluting the components contained in such complex under denaturing conditions after removing any unbound material.

The affinity tags useful in the invention include, but are not limited to, an amino acid recognition sequence of a biotin ligase, Glutathione-S-Transferase (Invitrogen), $His_6$ hexapeptide, STREP-TAG II™ (Sigma GenoSys), calmodulin binding peptide (CBP, KRRWKKNFIAVSMNRFK-KISSSGAL (SEQ ID NO: 10), Stratagene, La Jolla, Calif.) any number of available epitopes for which appropriate immunochemical reagents are available (for example, hemagglutinin (HA) (YPYDVPDYA (SEQ ID NO: 15), BD Biosciences, San Jose, Calif.), FLAG (DYKDDDD (SEQ ID NO: 3), Sigma Aldrich, St Louis, Mo.), Myc (EQKLISEEDL (SEQ ID NO: 12), Stratagene, La Jolla, Calif.), as well as polypeptides to which immunological or nonimmunological (e.g. aptamers) reagents can be prepared. The amino acid sequence of a biotinylation recognition sequence (e.g. AVI-TAG™) is particularly preferred since the affinity of biotin for streptavidin is one of the strongest noncovalent interactions known, allowing for highly specific binding of a biotin-tagged protein to an affinity matrix of immobilized streptavidin or suitable avidin-like molecule.

The removal tag (RT) is an affinity tag which facilitates the removal of the excess bait from the purified protein complex. Preferred removal tags are peptides which exhibit high affinity for metals such that the interacting proteins can be purified under denaturing conditions without dissociating the bait from the affinity matrix. Specifically exemplified herein is a hexapeptide $His_6$ which remains bound to nickel ($Ni^{2+}$) under denaturing conditions such as urea, guanidine or detergents (e.g., N-lauroylsarcosine (sarcosyl)). It is feasible that any tags with an affinity higher than typical non-covalent protein interactions, such as those involved in the formation of protein complexes or intramolecular forces involved in protein folding, can be used as removal tag. Thus the AVITAG™ system itself would be another example because of its high affinity for its affinity matrix.

The protease specificity sequences useful for the invention include, but are not limited to, TEV, PRESCISSION protease™ (Amersham Biosciences, Piscataway, N.J.), enterokinase, thrombin (Amersham Biosciences, Piscataway, N.J.), Factor Xa, and furins. Any amino acid sequence providing a recognition sequence for a protease having a high specificity is suitable for the invention. High specificity, as used herein, means that the protease cleaves only at the recognition sequence and that that recognition sequence is typically comprised of several amino acids or alternatively is specific to a unique secondary or tertiary structure formed by the recognition sequence.

Examples of the bait protein include, but are not limited to, proliferating cell nuclear antigen (PCNA, GENBANK™ Accession No. CR_541799), histone deacetylase 1 (HDAC1, GENBANK™ Accession No. NM_004964), cyclin-dependent kinase inhibitor 1b (CDKN1b, GENBANK™ Accession No. NM_004064), N-ethylmaleimide-sensitive factor attachment protein (NAPA, GENBANK™ Accession No. NM_003827), cyclin-dependent kinase 5 (CDK5, GENBANK™ Accession No. NM_004935), growth factor receptor-bound protein 2 (Grb2, GENBANK™ Accession No. NM_002086), eukaryotic initiation factor 4E (eIF-4E, NM_001968), cyclin D1 (GENBANK™ Accession No. NM_053056), v-abl Abelson murine leukemia viral oncogene homolog 1 (ABL-1, NM_005157), BCL2-like 1 (BCL2L1, NM_001191), RAD51 homolog (RAD51, NM_002875), retinoblastoma 1 (RB1, NM_000321), tumor protein p53 (TP53, NM_000546), transformed 3T3 cell double minute 2 (MDM2, NM_002392), Cas-Br-M (murine) ecotropic retroviral transforming sequence (CBL, NM_005188), ras homolog gene family, member A (ARHA, NM_001664) cyclin-dependent kinase inhibitor 3, (CDKN3, NM_005192), SUMO1/sentrin/SMT3 specific protease 2 (UBL1, NM_021627), SMT3 suppressor of mif two 3 homolog 3 (SMT3H1, NM_006936), neural precursor cell expressed, developmentally down-regulated 8, (NEDD8, NM_006156) SMT3 suppressor of mif two 3 homolog 2 (SMT3H2, NM_001005849), ubiquitin-conjugating enzyme E2I (UBE2I, NM_003345), chromobox homolog 3 (CBX3, NM_007276), PAI-1 mRNA-binding protein (PAI-RBP1, NM_015640), CDC37 cell division cycle 37 homolog (CDC37, NM_007065), protein tyrosine kinase 2 beta (PTK2B, NM_004103), protein tyrosine phosphatase, non-receptor type 11 (PTPN11-B, NM_002834), homocysteine-inducible, endoplasmic reticulum stress-inducible, ubiquitin-like domain member 1 (HERPUD1, NM_014685), ubiquitin-conjugating enzyme E2G 2 (UBE2G2, NM_003343), ubiquitin-conjugating enzyme E2L 3 (UBE2L3, NM_003347), HIV-1 integrase (integrase, AF324493).

The first binding component (i.e., modified bait protein) is prepared in vivo in a cell, or organism or in vitro or a combination of both. If the modified bait protein is expressed in a cell from which a desired protein complex is to be purified, those proteins and other cellular components with which it normally binds are purified together with the bait protein under conditions that do not disrupt the binding interactions between those proteins. Alternatively, the modified bait protein can be expressed in a transgenic animal and tissues from such animals or whole organisms themselves can be used in the invention to generate and to purify protein complexes. The first binding component can also be prepared recombinantly in bacteria or another host using methods well-known in the art. In this instance, the purified first binding component is mixed with a cell or tissue or organism lysate of choice to form a protein complex in vitro, which is then purified according to the steps described herein.

BRIEF DESCRIPTION OF THE DRAWINGS

FIGS. 4A-4B demonstrate the efficiency of TEV protease in cleaving the E24-tagged (A) and E25-tagged (B) fusion proteins bound to NEUTRAVIDIN™ beads. The starting uncleaved fusion proteins are shown (U) and the total available uncleaved fusion protein bound to beads (T) are shown as controls. White and black arrows indicate the cleaved fusion protein and TEV protease, respectively. TEV was used at two different concentrations (1×, 10×) as detailed in the Examples Section. Minus and plus signs refer to the absence or presence of cell lysate and thus bound interacting proteins.

The results shown in FIGS. 6 and 7A-7B demonstrate that the hexapeptide, $His_6$, contained in the E23-tagged protein serves as an efficient removal tag to remove excess bait significantly in one step by inclusion of the nickel affinity matrix in the pull-down procedure. These results also demonstrate that the efficiency of the mass spectrometric identification of the purified protein complexes can be significantly enhanced by the bait reduction step. In particular, FIGS. 7A and 7B show that the less the bait is detected, the more the interactors can be identified and that the identified interactors often have a higher score when the bait is reduced. The score is a measure of the confidence in the MS based identification. Generally, an increase in the score is an indicator of the improved purity, quantity or both, in the isolation of the protein complex.

DETAILED DESCRIPTION OF THE INVENTION

Figure 1:
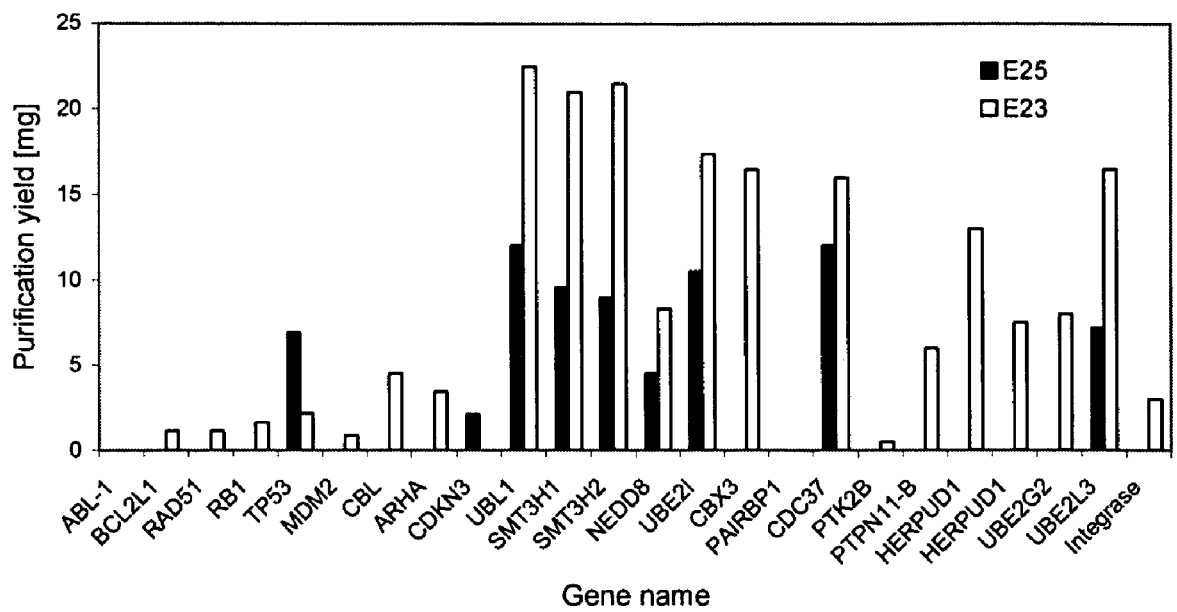
FIG. 1 shows the protein yield levels of multiple E23- and E25-tagged proteins (see the Examples section for details) derived from 1 Liter cultures of E coli transformants. The proteins were purified using Ni-NTA affinity purification as described in the Examples section. A majority of the bait proteins can be readily expressed at significant levels using the E23-, E24- or E25-tagged vectors disclosed herein.

In general, the terms and phrases used herein have their art-recognized meaning, which can be found by reference to standard texts, journal references and contexts known to those skilled in the art. The following definitions are provided to clarify their specific use in the context of the invention.

The term "protein complex", as used herein, designates a cluster of macromolecules comprising at least one protein wherein the cluster is stabilized by non-covalent bonds. A protein complex can be comprised entirely of proteins or peptides (referred herein as individual components), or it can include carbohydrates, lipids, glycolipids, nucleic acids, oligonucleotides, nucleoproteins, nucleosides, nucleoside phosphates, enzyme co-factors, porphyrins, metal ions and the like, or any biomolecule. The phrase "purified individual components", as used herein, is intended to mean that the individual components obtained by the methods of the invention are enriched relative to the starting material.

The term "bait" or "bait protein" is used synonymously herein and is generally a protein or peptide for which the nucleotide coding sequence is known in the art or is obtainable by employing methods well known in the art. In certain instances, the bait can be more than one protein or peptide. Any protein or a fragment thereof can serve as the bait. The invention does not require any knowledge of the function of the bait protein and can thus serve as a general purification strategy for purifying any protein complex. A bait can be a drug which has a biological activity and is predicted to bind another molecule to exert its activity. Examples include a small chemical molecule, a peptide, an oligonucleotide, a DNA or RNA, a carbohydrate, a polysaccharide, and the like.

The term "first binding component" is typically, but not necessarily, a protein, synonymously used as the "modified bait" herein. The first binding component possesses two properties significant for the invention: (a) it can bind to a protein or protein complex in a cell, or an intact organism, cell lysate or tissue lysate, and (b) it can bind to an affinity reagent or can be modified by attachment of an affinity ligand. Property (a) is an inherent biological property of the first binding component. Property (b) is conferred by adding to the native structure of the bait a peptide tail having multiple functional segments.

The first segment of the first binding component is an affinity tag (AT1 or first affinity tag). The affinity tag is generally an amino acid sequence which can specifically bind to a ligand, the GST-Glutathione pair, for example, or an amino acid sequence providing specificity for covalent attachment of an affinity ligand. Exemplified herein as AT1 are an amino acid sequence encoding GST and an amino acid sequence of a biotinylation recognition sequence, which can be recognized by a biotin ligase (e.g., BirA, an *E. coli* gene product, which may be endogenous or added exogenously) to covalently attach a biotin molecule to the peptide [Schatz P J *Biotechniques* (1993) 11:1138-43]. The use of the GST tag as a fusion partner for protein purification, especially when expressed recombinantly in *E coli*, has been described in Smith and Johnson [*Gene* (1988) 67:31-40]. The biotin moiety serves as an affinity ligand that specifically binds any avidin-like reagent with a high affinity for biotin, for example streptavidin or neutravidin, immobilized in a matrix usually in the form of a chomatography support or bead. In principle, any amino acid sequence providing recognition for attachment of an affinity ligand can be employed.

The second functional segment is termed as "protease specificity sequence" and contains an amino acid sequence providing a recognition site for a protease that specifically cleaves at or near the recognition sequence. Many specific proteases are known, together with their recognition sequences, including, but not limited to TEV protease (recognition sequence: Glu-Asn-Leu-Tyr-Phe-Gln-Gly (SEQ ID NO: 7), InVitrogen, Carlsbad, Calif.), PRESCISSION protease™ (recognition sequence: Leu-Glu-Val-Leu-Phe-Gln-Gly-Pro (SEQ ID NO: 9), Amersham Biosciences, Piscataway, N.J.), enterokinase (recognition sequence: Asp-Asp-Asp-Asp-Lys (SEQ ID NO: 15), Stratagene, La Jolla, Calif.), clotting factors such as Factor Xa (recognition sequence: Ile-Glu-Gly-Arg (SEQ ID NO: 4), Qiagen, Valencia, Calif.), furins (e.g. recognition sequence: Arg-Xaa-Lys/Arg-Arg (SEQ ID NO: 11), Calbiochem, San Diego, Calif.) and the like. It is preferred to employ the recognition sequence of a protease that does not cleave a peptide bond within the protein complex itself. (Parks, et al. Anal Biochem. 1994 Febuary 1;216(2):413-7.).

The third functional segment is termed as "removal tag" or "second affinity tag" (or AT2) and is generally a peptide having a sequence capable of being specifically bound to one or more ligands of an affinity matrix such as a chromatography support or bead with high affinity. An example of the removal tag or second affinity tag is a hexapeptide, $His_6$, which can bind to a column of nickel ($Ni^{2+}$) or cobalt ($Co^{2+}$) with high affinity. Hexahistidine, as exemplified herein has the desirable feature that it can bind its ligands under conditions that are denaturing to most proteins and disruptive to most protein-protein interactions. Thus it can be used to remove the bait protein tagged with hexahistidine following the disruption of protein-protein interactions with which the bait has participated. This liberates the bait from its interactions allowing removal of it, but not its interacting partners. Removal of the bait but not its interacting partners enriches for these partners and improves the ability for mass spectrometric analysis. In cases where the interacting partners are present at a low stoichiometry, bait removal may enable or improve their identification, as exemplified herein.

The first binding component can include one or more additional affinity tags which are typically peptides having an amino acid sequence capable of specifically binding to and eluting from one of more ligands of an affinity matrix such as a chromatography support or bead. Typical examples of a peptide affinity tag include an epitope, which can bind to a matrix-immobilized antibody, or a specific binding protein. Peptide affinity tags are those which are capable of being eluted from the affinity matrix under highly specific mild conditions unlikely to disrupt the protein complex or elute nonspecifically associated contaminants that interact tightly with the affinity matrix. An example is a hexapeptide $His_6$ which is known to specifically bind to a column of nickel ($Ni^{2+}$) or cobalt ($Co^{2+}$) with high affinity [Crowe et al. (1994)]. In *Methods in Molecular Biology* (Harwood, A. J., eds.). Vol. 31:371-387, Humana Press, Inc. Otawa; Porath et al. (1992) *J. Protein Expr. Purif.* 3: 263-281], which can be specifically eluted with imidazole, for example. Alternatively, the same hexapeptide can be used under denaturing conditions to specifically remove some or all of the first binding component.

Another example of a peptide affinity tag is a 12 amino acid peptide, known as the Protein C tag in the art, which is recognized in a calcium dependent manner by the commercially available monoclonal antibody HPC4 (Roche Applied Science, Indianapolis, Ind.). Other examples of affinity tags are the FLAG M1™ (Sigma Corp., St. Louis, Mo.) epitope and calmodulin binding peptide (CBP), whose respective affinity interactions are reversibly $Ca^{+2}$ dependent. The third functional segment can also be composed of two or more affinity tags in tandem that may or may not be separated from each other by specific proteolytic sites that are different from that adjacent to the affinity modifiable segment. When the third functional segment is composed of multiple affinity tags they can be used in alternative or sequential affinity purification steps. When greater purity is desired, sequential affinity purification steps can be used. Alternative affinity purification steps can allow for customization of the purification depending on the bait.

The functional segments described above are included in a single linear peptide bound to the bait with the removal tag (or additional affinity tag) positioned proximal, but not necessarily adjacent to the bait. If the bait is itself a protein, the modifying peptide segment can be present as an extension of the amino terminus or the carboxy terminus of the bait or at both termini. Alternatively, one or more affinity tags can be inserted in the ORF of the bait. When the combined tags are present on the same side of the bait (each N-terminal, or each C-terminal), the functional segments of the modifying peptide are arranged in sequence, with the removal tag (or additional affinity tag) being proximal to, although not necessarily adjacent to, the bait followed by the protease specificity sequence, if necessary, then by the affinity tag (e.g., affinity modifiable segment or an affinity tag such as GST), the latter being most distal. Alternatively, the removal tag itself may be the affinity modifiable segment (e.g. Avitag). It is desirable that the modifying peptide be short, to minimize any effect it may have on normal binding properties of the bait to the protein complex. This is exemplified by the AviTag containing construct described herein, which is significantly smaller than other tandem affinity tags described in the prior art. The invention can also be practiced with the same affinity tag serving as the affinity segment more than once. For example, the same tag (e.g., $His_6$) can be used as the affinity tag prior to being used as the removal tag. Similarly, if the affinity tag is present in more than one copy, for example with one copy on either side of the cleavage site or either side of the bait protein, the same affinity tag can be used more than once. In some cases it may be desirable to place tags at both the N and C-terminus with protease digestion sites located between the "bait" and the tags.

The term "second binding component", as used herein, refers to a protein complex comprising the removal tag (or additional affinity tag) and a bait bound to the protein complex which is formed after a specific protease digestion.

The present invention relates to efficient methods for purifying protein complexes and the components comprising the complex from a cell, a cell or tissue lysate or an organism, or organism lysate by employing the first binding component described herein. The first binding component contains one or more affinity tags including a removal-tag placed proximal to the bait, separated by an amino acid sequence encoding a specific protease recognition site in such a way that more than one round of affinity purification can be carried out, if necessary. An optimum protease cleavage step may be employed between one or more of the purification steps and the individual components can be separated from the bait using a matrix specific for the removal tag under appropriate conditions.

The isolation and identification of proteins bound to an exogenous bait protein introduced at relatively normal expression levels in cells, tissues or organisms has been a challenging problem. The need to express the bait at low levels in order to avoid the introduction of aberrant interactions, creates a situation where small amounts of protein are isolated from large numbers of cells ($10^8$ to $10^{10}$) or equivalent cell or tissue lysate and thus in the presence of an abundance of contaminants. The present invention solves this problem by incorporating a combined set of affinity tags that utilize high affinity, specificity and ease of elution. Disclosed herein, are a new combination of existing affinity tags that when combined are ideal for this application. In particular, we describe the use of biotin ligase recognition sequences that are small, allow for extremely high affinity isolation and introduce a minimal background due to low levels of endogenous ligands. Biotin ligase or biotinylation recognition sequences, in combination with protease recognition sequences and additional optional affinity tags create ideal constructs for the applications described.

Here is general design of the first binding component:

$1^{st}$ segment (affinity tag)—$2^{nd}$ segment (a specific proteolytic cleavage site)—$3^{rd}$ segment (optional one or more specific affinity tags with or without another proteolytic cleavage site between them and/or the bait)—(bait).

An example of the invention is the biotin-avidin system which uses an affinity modifiable segment as the first segment. Specifically, the system involves the incorporation of a biotinylation recognition sequence (can be any one of a number of amino acid sequences specifically recognized and biotinylated by members of the biotin ligase family of enzymes), followed by a specific protease digestion site and then finally a hexapeptide $His_6$ tag. However, the third functional segment can be one or more specific peptide sequences that can serve as affinity tags including the removal tag, e.g., the Protein C tag, STREP-TAG II™(Sigma GenoSys), Hemagglutinin (HA) tag or FLAG recognition sequence. The biotinylation recognition sequence can be a short peptide or a protein containing natural or unnatural amino acid sequences that can be biotinylated by a specific biotin ligase in vivo or in vitro.

The following are examples of the first binding component:

(Biotinylation recognition sequence)-(TEV protease site)-($His_6$)-(bait), (Biotinylation recognition sequence)-(TEV protease site)-(Protein C tag)-(bait) or (Glutathione-S-Transferase)-(thrombin and/or PRESCISSION™ cleavage site)-($His_6$)-(bait protein).

In the above examples, a hexapeptide $His_6$ and/or the Protein C tag, is used as the peptide affinity tag or removal tag.

The Protein C tag is a 12 amino acid peptide recognized in a calcium dependent fashion by the monoclonal antibody HPC4 (Roche, Indianapolis, Ind.). Additionally, the Protein C tag can be placed at the N or C-terminus of a protein or internally and still be recognized by HPC4. For this reason, a wide selection of protease cleavage sites can be incorporated and still permit purification using HPC4. It also means that a single antibody can be used for both the initial purification of the modified bait protein and the subsequent second-step purification of the multi-protein complex. In the above examples, the TEV protease site is used as one of many possible proteases. In general, since this design is flexible with regard to the type of protease used, it is advisable to select a highly specific protease, such as the TEV protease, to reduce inappropriate proteolysis.

The principle of the invention where the second affinity tag serves as the removal tag is further illustrated in the following flow chart.

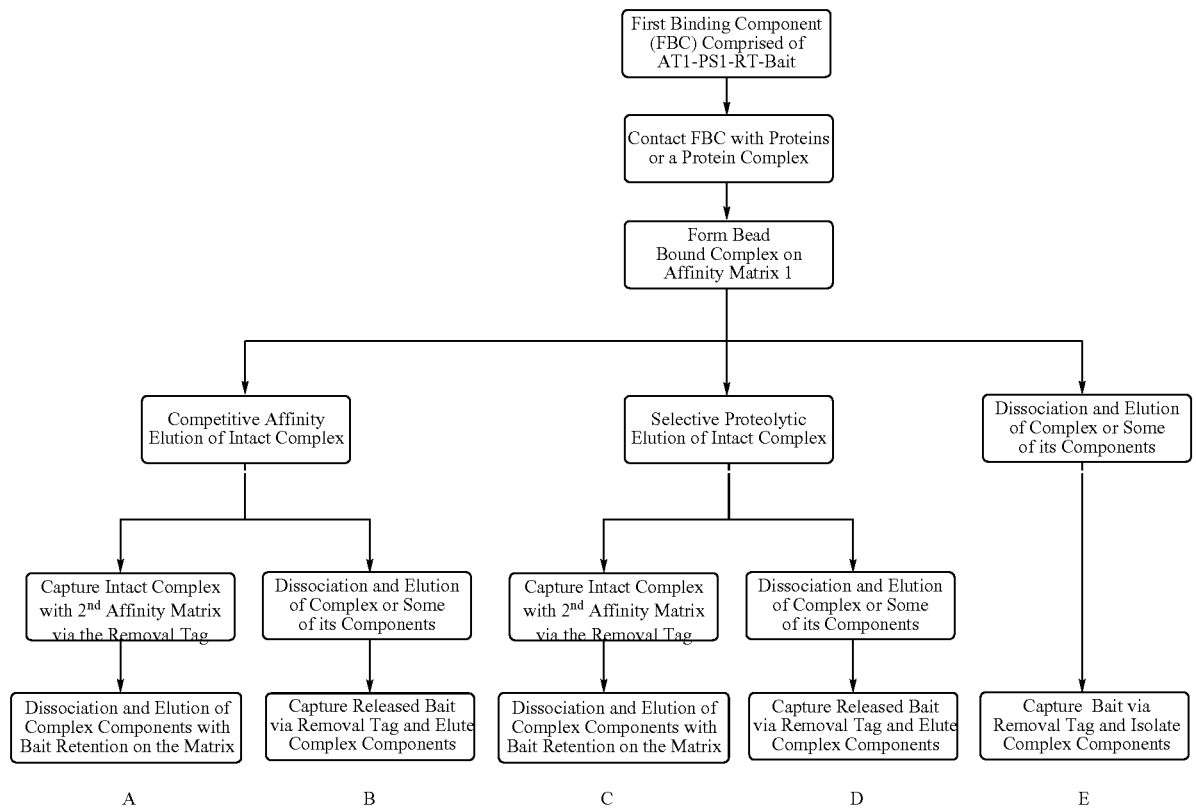

The flow chart shown above provides examples of how a protein complex and individual components contained in such protein complex can be purified either in an in vivo or in vitro pull-down assay. The term "pull-down" assay, as used herein, refers to the method of purification of the invention. A protein complex formed with the first binding component is initially bound to a matrix specific for one of the affinity tags and washed sufficiently to remove unbound material. The individual components contained in a given complex can be purified by one of the five ways as indicated as A-E in the flow chart:

The intact bait-bound protein complexes are released from the matrix by either proteolytic cleavage (C and D) or specific elution (A and B). E represents a case where the complex bound FBC can be directly dissociated from the first affinity matrix under generally denaturing conditions (e.g., using chaotropic agents such as urea, guanidine, or detergents) or by more specific dissociating conditions, including but not limited to using a salt or temperature gradient, whereby either the entire complex or some of its individual components are obtained in one step. In this instance, the individual components may be further purified from the mixture if necessary by selective capturing of the bait via a removal tag and elution of the components. The intact bait-bound protein complexes released from the matrix by selective affinity elution (A and B) and the complexes which have been released from the matrix via digestion with a specific protease (C and D) are subjected either to binding to a second affinity matrix, followed by dissociation and elution of the components with the bait bound on the matrix (A and C), or, alternatively, to dissociation and elution of some of its components, followed by binding the bait to the second affinity matrix to remove excess bait (B and D).

The bait portion of the first binding component can be any protein or a fragment thereof. When the nucleic acid sequence encoding such protein or the fragment thereof, is known, a priori, the first binding component can be prepared by standard cloning procedures known to those in the art. Alternatively, the first binding component could be prepared from cDNA libraries, or the like, without prior knowledge of the bait nucleic acid sequence. During such a "random" or "shotgun" approach, the identity of the bait protein could be determined later by mass spectrometry or other methods known in the art. It should be noted that the method of the present invention where the first binding component contains a removal tag is designed to enrich the interacting proteins by depleting the bait as much as possible. The depletion is often not complete. Thus some amount of bait will generally be identified allowing this invention to be practiced even for the "random" or "shotgun" approach.

Following is a list of bait proteins that have been used to illustrate the invention, together with some of the proteins likely to be isolated as part of a protein complex isolatable by the method of the invention. The proteins are listed by the standard names by which they are known in the art, and by which they are indexed in public databases, i.e., GENBANK™. For a more complete list of interacting proteins isolated, see Table 3 below.

1. Grb2: (NM 002086) can serve as bait for Sos1, Shc, dynamin2
2. NAPA: (NM 003827) can serve as bait for syntaxins, VAMP, SNAP-23
3. CDKN1b: (NM 004064) can serve as bait for CDC2, CDK2, Grb2

For the purpose of further illustration, the following additional bait proteins are noted, together with some of the proteins likely to be isolated as part of a protein complex isolatable by the method of the invention.

4. eIF-4E: (NM 001968) can serve as bait for purifying a protein complex that includes eIF-4A, eIF-4GI, MNK2, eIF-3 (itself a ten-subunit complex), ERK1/2.
5. Cyclin D1 (CCND1): (NM 053056) can serve as bait for purifying a protein complex that includes CDK4, PCNA, p21/Cip1 (CDKN1A).
6. PCNA: (NM 002592) can serve as bait for Hus1, Rad9.

The first binding component can be prepared either in vivo or in vitro or a combination thereof. Once a construct capable of expressing a desired bait protein with the appropriate modifications is prepared, the modified bait protein can be expressed in prokaryotic cells (e.g., *E. coli*) by employing the standard protocols well known in the art [Makrides, S. C. (1996) *Microbiol. Rev.* 60:512-538; Baneyx, F. (1999) *Curr. Opin. Biotech.* 10:411-421]. The first binding component containing the GST and $His_6$ tags as exemplified herein is particularly convenient since it can be expressed as soluble protein in *E. coli* and readily purified using the GST or $His_6$ tag. Alternatively, the first binding component can be expressed in eukaryotic cells (e.g., mammalian cells or yeast) [Logan A. C. et al. (2002) *Curr. Opin. Biotechnol.* 13:429-436; Regulier, E. (2002) *Hum Gene Ther.* 13:1981-1990; Geisse, S. et al. (1996) *Protein Expression and Purification* 8:271-282]. Finally, the first binding component can be expressed in an organism by transgenic or "knock-in" methods, as known in the art.

When the first binding component is prepared in a recombinant host (e.g., *E. coli*), purification of the recombinantly expressed protein could be performed efficiently using the affinity tag (e.g., GST or $His_6$) contained therein by employing the standard biochemical approaches (e.g., beads/column containing Glutathione or $Ni^{2+}$). In this case it is preferable to retain all three functional segments. If biotinylation of the bait protein has not occurred during expression in the recombinant host organism, it can then be performed, in vitro, using a recombinantly expressed and purified product of the *E. coli* BirA biotin ligase gene, for example. In this scenario, the purified first binding component could then be mixed with a source of protein complex, such as a cell lysate, tissue lysate or organism lysate. Alternatively, the first binding component can be mixed with a source of protein complex, and then the complex bound first binding component is subjected to biotinylation in vitro.

The modified bait protein can also be expressed in cells or an organism containing possible ligands and possibly biotinylated in the cell or organism by an endogenous or exogenous biotin-ligase, expressed normally or recombinantly introduced. This system is thus applicable for experiments where the modified, biotinylated bait is expressed in cells of many types (prokaryotic or eukaryotic). Mammalian cells or whole organisms (e.g. mice transgenic for the tagged first binding component) would offer an added advantage since they allow the isolation of multi-protein complexes after their formation, in situ. An example of the use of a biotin tag and endogenous biotinylation in mammalian cells can be found in [Pyrrott M. B. et al. (2001) BBRC 281:993-1000; Pyrrott M. B. et al. (2002) *Mol Ther*. 1:96-104]. The biotin-tagged proteins, together with associated ligands of protein complexes, are isolated from the cell, tissue or organism lysates using an avidin-like affinity reagent. Specific elution of biotin-tagged proteins from the affinity column is then performed by digestion with a protease (e.g. TEV protease). At this stage the digestion step can serve several purposes: (1) it allows the specific elution of the bait and the associated protein complexes for immediate analysis with or without removal of the bait. The immediate analysis of the eluate from the first purification step may be advantageous for the identification of transiently interacting proteins that would normally be lost during multi-step purifications. The extremely high affinity interaction of biotin-avidin enables this rapid analysis because complexes are isolated and concentrated more quickly and survive very swift, yet stringent washing prior to elution; (2) it can expose a second affinity tag, hitherto cryptic or sterically hindered, for use in a second round of purification; (3) or create the specificity required for the second step. When a $His_6$ sequence is used as the removal tag, nickel-chelate bound beads allow for a second affinity purification step to remove contaminants remaining after the protease digestion or after elution by more standard approaches. The $His_6$ tag is particularly useful since all or some of the bait protein can be removed under certain denaturing conditions prior to mass spectrometry analysis, because the $His_6$-$Ni^{+2}$ interaction survives relatively strong denaturing conditions. It should also be noted that use of "bait removal" is still compatible with the identification of transient interactors as described above, since their dissociation during the procedure results in their addition to the "free pool" of interactors that will be analyzed by MS and it is unlikely under denaturing conditions for them to bind to the second affinity support. If a FLAG sequence is used as the affinity tag, a cryptic epitope can be created that is exposed upon the protease digestion step. The digestion can create an N-terminal FLAG sequence that is specifically recognized by a calcium dependent antibody (e.g., SIGMA FLAG M1™). This antibody does not recognize the FLAG sequence if it is internal or C-terminal. In the presence of calcium, a second purification step can be done with immobilized anti-FLAG M1™ antibody. The specific proteins can then be isolated by a second specific and gentle elution with a calcium chelator such as EGTA. Ideally, when combined with a FLAG epitope, the digestion sites should incorporate a sequence recognized by a protease that cleaves C-terminally and "exo" to its recognition sequence, i.e., between the recognition sequence and the peptide affinity tag. Examples of this include enterokinase, Factor Xa and furins. Additionally, it is possible to use proteases that do not cleave "exo" to their recognition sequence, if the amino acids left behind following cleavage are part of or compatible with the FLAG M1 recognition sequence. A third example of an affinity tag is the Protein C epitope (Roche, Indianapolis, Ind.) which is also recognized by a calcium dependent antibody. Since this epitope is not sensitive to its location (can be N-terminal, C-terminal or internal), this design is more flexible with regards to the protease used following the first affinity purification step.

The present invention has several characteristics that distinguish it from the conventional methods [Puig O. et al. (2001) *Methods* 24:218-229]. The first distinguishing feature of the invention is the use of the biotin-streptavidin or GST-Glutathione interaction for the first step in the isolation of a complex bound to the bait. The biotin-streptavidin interaction is seven orders of magnitude higher in affinity than the protein A-IgG system used in the tandem affinity purification (TAP) protocol of Puig et al. ($K_d$ of one Z domain binding to IgG is approximately $10^{-8}$M [Braisted and Wells, (1996) *Proc. Natl. Acad. Sci.* USA. 93:5688] vs. a $K_d$ of $10^{-15}$ M for biotoin-streptavidin). This is critical because the first purification step requires the isolation of the protein complex when it is in its most dilute and contaminated state. The high binding affinity allows the isolation of biotinylated protein and associated ligands present at femtomolar or higher concentrations and permits a very stringent wash (if necessary) without loss of bait protein. As discussed above, this also allows rapid isolation and concentration of protein complexes, minimizing losses of specific interactors and potentially enabling the analysis of transiently interacting proteins. The published protein A-IgG system would only allow the isolation of proteins present at several logs higher concentration and wouldn't allow as rapid an analysis or permit the use of such a stringent wash. Another improvement over the protein A-IgG system is that the consensus biotinylation sequences are short and thus potentially less disruptive to protein folding during bait expression and to subsequent protein-protein interactions. If the FLAG tag is used to practice the invention, this represents a system where the successful digestion with the protease can create a unique recognition sequence for the second purification step which can be advantageous in creating additional specificity and flexibility during the second purification step. For example, nonspecifically bound proteins that are cleaved and/or otherwise eluted during the digestion step are unlikely to meet the criteria for binding to the second affinity support. There are three anti-FLAG antibodies commercially available (M1, M2, M5, Sigma Corporation, St Louis, Mo.). Only the M1 antibody binds the FLAG sequence in a calcium dependent fashion and thus allows a specific and gentle elution. M1 recognizes sequences as small as DYKD (SEQ ID NO:1) or DYKDE (SEQ ID NO:2), but binds to such sequences only when they are present on the N-terminus (unblocked by an initiation Methionine or any other amino acid). Thus, the FLAG sequence can be used with any protease that cleaves exo and C-terminal to its recognition site, thereby allowing the digestion dependent creation of an N-terminal FLAG sequence from a previously M1 unreactive internal FLAG sequence. Tags such as $His_6$ and FLAG are also advantageous over biologically relevant tags such as CBP (used in combination with the protein A-Z domains system in Puig et al.), which can bind to calmodulin and calmodulin-containing protein complexes naturally present in cells, cell lysates or tissue lysates, complicating their use. Affinity tags such as $His_6$, FLAG and others previously mentioned do not interact as extensively with biologically relevant and promiscuous ligands like calmodulin. Additionally, the use of CBP may require the incorporation of EGTA to prevent CBP-calmodulin interactions during the binding reaction and isolation of the protein complexes. Under these circumstances, the CBP containing constructs are not compatible with interactions requiring calcium and other divalent metal ions. Affinity tags such as $His_6$, FLAG and the others previously mentioned can be used in the presence of calcium, thus permitting the identification of calcium dependent interactions. Finally, $His_6$ and FLAG are shorter peptides than CBP and thus potentially less disruptive in protein-protein interactions. Another characteristic is the use of a removal tag to separate the excess bait from the purified protein complex prior to subjecting the complex to analysis for identification of its components. This feature is particularly useful when the mass spectrometric analyses are employed to identify the interacting proteins contained in the purified protein complex since a large excess of bait protein is used in the pull-down process, which masks the interacting proteins present at low concentrations in the purified complex. Specifically exemplified herein is a hexapeptide $His_6$ as removal tag. It is known that the $His_6$-nickel interaction is stable under conditions that are mildly denaturing to proteins and/or disrupt protein-protein interactions. The use of $His_6$ as the removal tag allows for a preferential elution of the unknown protein interactors over that of the first binding component which is often present in large excess relative to the amount of the protein interactors. For this purpose, one can use any art-known protein denaturing conditions such as urea, guanidine or a detergent (e.g., N-lauroylsarcosine). The removal of the excess bait results in enrichment of the interacting proteins which facilitates identification of the proteins by mass spectrometric analyses.

The proteins or fragments thereof contained in the purified protein complexes can be characterized further by employing standard techniques that are known in the art. For example, the individual proteins that comprise the complexes purified according to the invention are identified by a variety of mass spectrometric methods which include an associated set of separation methods. Most current generations of mass spectrometers enable the rapid identification of known proteins by searching mass spectrometry data (peptide masses, and/or peptide fragment mass spectra) against a database of known sequences (predicted peptide masses and/or predicted peptide fragment mass spectra). Alternatively, it is becoming much more routine to also be able to identify de novo amino acid sequences of peptides directly from peptide mass spectra and thus discover unknown proteins. In many cases, components of a protein complex would not have previously been isolated and may be known to exist only from genetic studies, or they can be previously unknown or known but unrecognized as components of a complex that interacts with the bait. The method of the invention therefore serves as a method for isolating, purifying and characterizing novel proteins and for providing insight into their biological function. In addition, protein complexes isolated by the method of the invention under varied physiological or pathological states will yield data as to how the composition of a complex varies in response to varied conditions. The data are then used as indicators of disease, as indicators of therapeutic efficacy, and for providing a rationale for novel therapies. Identifying novel proteins or novel interactions of known or novel proteins can lead to the identification of new members of disease-associated pathways or biochemical reactions. These proteins can be drug targets because of their interaction in such pathways or reactions whether or not they vary according to the "states" described above.

The following is the summary of the amino acid recognition sequences described herein with their sequence identifier numbers.

| SEQ ID NO. | Sequence | Description |
| --- | --- | --- |
| 1. | DYKD | M1 recognition sequence |
| 2. | DYKDE | M1 recognition sequence |
| 3. | DYKDDDD | M1 recognition sequence |
| 4. | IE/DGR | Factor Xa recognition sequence |
| 5. | EDQVDPRLIDGK | Protein C tag |
| 6. | MSGLNDIFEAAQKIEWHE | BirA recognition sequence |
| 7. | ENLYFQG | TEV protease recognition sequence |
| 8. | HHHHHH | hexahistidine, $His_6$ |
| 9. | LEVLFQGP | PRESCISSION ™ recognition sequence |
| 10. | KRRWKKNFIAVSAANRFKKISSSGAL | Calmodulin binding peptide (CBP) |
| 11. | RXK/RR | Furin |
| 12. | EQKLISEEDL | Myc |
| 13. | YPYDVPDYA | Hemagglutinin (HA) |
| 14. | LVPRGS | thrombin |
| 15. | DDDDK | enterokinase |

DNA constructs prepared for introduction into a prokaryotic or eukaryotic host will typically comprise a replication system (i.e. vector) recognized by the host, including the intended DNA fragment encoding the first binding component of the present invention, and will preferably also include transcription and translational initiation regulatory sequences operably linked to the polypeptide-encoding segment. Expression systems (expression vectors) may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides may also be included, where appropriate, from secreted polypeptides of the same or related species, which allow the protein to cross and/or lodge in cell membranes, or be secreted from the cell.

An appropriate promoter and other necessary vector sequences will be selected so as to be functional in the host. Examples of workable combinations of cell lines and expression vectors are described in [Sambrook et al. (1989) vide infra; Ausubel et al. (Eds.) (1995) *Current Protocols in Molecular Biology*, Greene Publishing and Wiley Interscience, New York; and Metzger et al. (1988) *Nature* 334:31-36]. Many useful vectors for expression in bacteria, yeast, fungal, mammalian, insect, plant or other cells are well known in the art and may be obtained from vendors such as InVitrogen, Stratagene, New England Biolabs, Promega Biotech, and others. In addition, the construct may be joined to an amplifiable gene (e.g., DHFR) so that multiple copies of the gene may be made. For appropriate enhancer and other expression control sequences, see also *Enhancers and Eukaryotic Gene Expression* (1983) Cold Spring Harbor Press, N.Y. While such expression vectors may replicate autonomously, they may less preferably replicate by being inserted into the genome of the host cell.

Expression and cloning vectors will likely contain a selectable marker, that is, a gene encoding a protein necessary for the survival or growth of a host cell transformed with the vector. Although such a marker gene may be carried on another polynucleotide sequence co-introduced into the host cell, it is most often contained on the cloning vector. Only those host cells into which the marker gene has been introduced will survive and/or grow under selective conditions. Typical selection genes encode proteins that (a) confer resistance to antibiotics e.g., kanamycin, tetracycline, etc. or other toxic substances; (b) complement auxotrophic deficiencies; or (c) supply critical nutrients not available from complex media. The choice of the proper selectable marker will depend on the host cell; appropriate markers for different hosts are known in the art.

Recombinant host cells, in the present context, are those which have been genetically modified to contain an isolated DNA molecule of the instant invention. The DNA can be introduced by any means known to the art which are appropriate for the particular type of cell, including without limitation, transformation, lipofection, electroporation or viral mediated transduction.

A DNA construct capable of enabling the expression of the first binding component of the invention or the nucleic acids encoding individual segments of the first binding component (e.g., affinity tags or protease recognition sequence) can be easily prepared by the art-known techniques such as cloning, hybridization screening and PCR. Polymerase Chain Reaction (PCR) is a repetitive, enzymatic, primed synthesis of a nucleic acid sequence. This procedure is well known and commonly used by those skilled in this art [see Mullis, U.S. Pat. Nos. 4,683,195, 4,683,202, and 4,800,159; Saiki et al. (1985) *Science* 230:1350-1354]. PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Since the extension product of each primer can serve as a template for the other primer, each cycle essentially doubles the amount of DNA template produced in the previous cycle. This results in a rapid accumulation of the specific target fragment, up to several million-fold in a few hours. By using a thermostable DNA polymerase such as Taq polymerase, which is isolated from the thermophilic bacterium *Thermus aquaticus*, the amplification process can be completely automated. Other enzymes which can be used are known to those skilled in the art.

Once a protein complex is purified according to the invention, a person of ordinary skill in the art can prepare monoclonal or polyclonal antibodies specific for the complex or the proteins contained in the complex. Monoclonal or polyclonal antibodies, preferably monoclonal, specifically reacting with a protein of interest can be made by methods well known in the art [see, e.g., Harlow and Lane (1988) *Antibodies: A Laboratory Manual*, Cold Spring Harbor Laboratories; Goding (1996) *Monoclonal Antibodies: Principles and Practice*, 3rd ed., Academic Press, San Diego, Calif.; and Ausubel et al. (1993) *Current Protocols in Molecular Biology*, Wiley Interscience/Greene Publishing, New York, N.Y.].

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1-4, Plenum Press, New York; and Ausubel et al. (1992) *Current Protocols in Molecular Biology*, Greene/Wiley, New York, N.Y.

EXAMPLES

The following examples are provided to illustrate the invention but are in no way intended to limit the scope of the invention. Three expression vectors used herein are termed as E23-tag, E24-tag, and E25-tag, and contain the nucleotide sequences capable of expressing a fusion protein (i.e., first binding component) of the following design:

E23: GST-thrombin-PRESCISSION™ cleavage site-His$_6$-Gly$_4$Ser-(bait protein)
E24: AVITAG™-TEV cleavage site-His$_6$-PrC-(bait protein)
E25: AVITAG™-(G$_4$S)$_2$-TEV cleavage site-His$_6$-PrC-(bait protein)

Where
GST=Glutathione-S-transferase
AVITAG™=BirA recognition sequence
PrC=Protein C epitope tag
Thrombin=thrombin protease recognition site
TEV=TEV protease recognition sequence Since all three constructs contain His$_6$ tag, as well as, either AVITAG™ (E24 and E25) or GST tag (E23), either tag in a given construct can be utilized for the purification of the fusion protein from the recombinant host cells in one step or a two-step purification described herein if needed.

Example 1

Construction of Expression Vectors

The *E. coli* expression vectors E23, E24 and E25 are based on the Invitrogen Gateway compatible vector pDEST15 (Cat# 11802-014) in which transcription is driven by the T7 promoter and which contain the sequence encoding Glutathione-S-Transferase (GST) at the N-terminus. PCR products amplified from M07 (see Example 11) were inserted into vector E04 which is a modified version of pDEST15 (expression vector which encodes a GST fusion domain, Invitrogen, Carlsbad, Calif.) containing a tag for GST and CBP (calmodulin binding peptide) separated by a cleavage site for PRESCISSION™ protease. E04 was made using the following PCR primers, GGAACCGGTGAAGGAGATAGAAC-CATGTCCCCTATACTAGGTTATTG-PinAI-SD-GST-F (SEQ ID NO: 16); TCCCTCGAGCCTGGTACCGAAAGT-GCCCCGG-XhoI-CBP-R (SEQ ID NO: 17), to amplify pGEX4T3/TAP (Amersham Biosciences, Piscataway, N.J.). Vector pGEX4T3/TAP and the PCR product were both digested with PinA1 and Xho I and ligated together.

Bacterial expression vector E23 was derived from expression vector E04. E04 consists of an N-terminal TAP tag of GST-PS-CBP. In order to alter the tags in E04 to those desired in E23 (GST-PS-HIS-G$_4$S) it was necessary to replace the CBP region with a HexaHis tag and a Gly$_4$Ser spacer region. This was achieved by amplifying the GST-Precission region of E04 by use of the polymerase chain reaction (PCR) using two primers. The first primer (T7 promoter primer) bound 50 bp upstream of a unique Nde I restriction site (CATATG) which marks the ATG start codon of the GST gene. The 3' primer was designed so that it contained 33 bp at its 3' terminus that were identical to the 3' end of the GST-PS region of E04, the 5' region of this primer (47 bp) encoded the HexaHis and G$_4$S region and a unique Xho I restriction site (CTCGAG) (see below and SEQ ID NOs: 18 and 19).

```
                   ProAsnSerLeuGluValLeuPheGlnGlyProHisHisHisHisHisHisGlyGlyGlyGlySerLeuGlu
3'. CCGAATTCCCTGGAAGTTCTGTTCCAGGGACCTCATCACCATCACCATCACGGTGGTGGCGGTTCCCTCGAGCG
      ATCGAT 5'                                                                    Xho I
```

The 837 bp PCR amplicon produced by these two primers was digested with Nde I and Xho I and ligated into E04 previously restricted with the same restriction enzymes in order to remove the existing GST-PS-CBP tags. The resultant progeny plasmids (E23) were screened and verified by DNA sequencing to confirm the correct arrangement of the tags and that they were in-frame with the attR1 gateway recombination site downstream.

Construction of E24 and E25 was achieved by amplifying the tag region of M07 (see Example 11) with the following oligonucleotide and MACH.Reverse (see Example 11). MACH.Nde—(purchased from MWG, High Point, N.C.)

5'-CTACCGGTGAAGGAGATAGT<u>CATATG</u>TCCGGCCTGAACGAC-3' (SEQ ID NO:20). This primer binds to the region around the ATG start codon of Avitag and introduces an Nde I site (underlined) over the start codon. Using these primers with M07 as the PCR template, the tag region of each vector was amplified with the replacement of the ps region with the Protein C region. The resultant PCR amplicons were digested with Nde I and Xho I and sub-cloned into NdeI/XhoI digested vector pD15-E04 and transformed into DB3.1 bacterial cells. Positive colonies were identified and verified by DNA sequencing.

Upon Sequencing of potential E25 clones it was discovered that a PCR error had deleted one of the $G_4S$ triplets in such away that it left a $G_4S$ doublet instead of the expected triplet. However, the $G_4S$ doublet is still in-frame with the downstream regions and so was named E25. Upon sequencing of a second batch of E25 clones a correct version containing the $G_4S$ triplet was identified and this was named E26.

The nucleotide sequences of the tag region (from the start of the ORF to the beginning of the bait protein) in the E23, E24 and E25 vectors are as follows:

E23-TAG (SEQ ID Nos: 21 and 22)

```
GST
MetSerProIleLeuGlyTyrTrpLysIleLysGlyLeuValGlnProThrArgLeuLeu
ATGTCCCCTATACTAGGTTATTGGAAAATTAAGGGCCTTGTGCAACCCACTCGACTTCTT

LeuGluTyrLeuGluGluLysTyrGluGluHisLeuTyrGluArgAspGluGlyAspLys
TTGGAATATCTTGAAGAAAAATATGAAGAGCATTTGTATGAGCGCGATGAAGGTGATAAA

TrpArgAsnLysLysPheGluLeuGlyLeuGluPheProAsnLeuProTyrTyrIleAsp
TGGCGAAACAAAAAGTTTGAATTGGGTTTGGAGTTTCCCAATCTTCCTTATTATATTGAT

GlyAspValLysLeuThrGlnSerMetAlaIleIleArgTyrIleAlaAspLysHisAsn
GGTGATGTTAAATTAACACAGTCTATGGCCATCATACGTTATATAGCTGACAAGCACAAC

MetLeuGlyGlyCysProLysGluArgAlaGluIleSerMetLeuGluGlyAlaValLeu
ATGTTGGGTGGTTGTCCAAAAGAGCGTGCAGAGATTTCAATGCTTGAAGGAGCGGTTTTG

AspIleArgTyrGlyValSerArgIleAlaTyrSerLysAspPheGluThrLeuLysVal
GATATTAGATACGGTGTTTCGAGAATTGCATATAGTAAAGACTTTGAAACTCTCAAAGTT

AspPheLeuSerLysLeuProGluMetLeuLysMetPheGluAspArgLeuCysHisLys
GATTTTCTTAGCAAGCTACCTGAAATGCTGAAAATGTTCGAAGATCGTTTATGTCATAAA

ThrTyrLeuAsnGlyAspHisValThrHisProAspPheMetLeuTyrAspAlaLeuAsp
ACATATTTAAATGGTGATCATGTAACCCATCCTGACTTCATGTTGTATGACGCTCTTGAT

ValValLeuTyrMetAspProMetCysLeuAspAlaPheProLysLeuValCysPheLys
GTTGTTTTATACATGGACCCAATGTGCCTGGATGCGTTCCCAAAATTAGTTTGTTTTAAA

LysArgIleGluAlaIleProGlnIleAspLysTyrLeuLysSerSerLysTyrIleAla
AAACGTATTGAAGCTATCCCACAAATTGATAAGTACTTGAAATCCAGCAAGTATATAGCA

TrpProLeuGlnGlyTrpGlnAlaThrPheGlyGlyGlyAspHisProProLysSerAsp
TGGCCTTTGCAGGGCTGGCAAGCCACGTTTGGTGGTGGCGACCATCCTCCAAAATCGGAT

Thrombin                 Precission                6 X His Tag
LeuValProArgGlySerProAsnSer  LeuGluValLeuPheGlnGlyPro   HisHisHis
CTGGTTCCGCGTGGATCCCCGAATTCC  CTGGAAGTTCTGTTCCAGGGACCT   CATCACCAT (G4S) Spacer
HisHisHis  GlyGlyGlyGlySer
CACCATCAC  GGTGGTGGCGGTTCC
```

E24-TAG (SEQ ID NOs: 22 and 23)

```
AVITAG ™
MetSerGlyLeuAsnAspIlePheGluAlaGlnLysIleGluTrpHisGlu  GlyAlaIleSerAla
ATGTCCGGCCTGAACGACATCTTCGAGGCTCAGAAAATCGAATGGCACGAA  GGCGCGATATCCGCG

TEV CLEAVAGE SITE                     6x His tag                Protein C
GluAsnLeuTyrPheGlnGly  SerSerAla  HisHisHisHisHisHis  GlySer  GluAspGln
GAGAACCTGTACTTCCAGGGC  AGCAGCGCT  CATCACCATCACCATCAC  GGGAGC  GAAGATCAG ValAspProArgLeuIleAspGlyLys
GTAGATCCACGGTTAATCGATGGTAAG
```

E25-TAG (SEQ ID NOs: 24 and 25)

```
AVITAG ™
MetSerGlyLeuAsnAspIlePheGluAlaGlnLysIleGluTrpHisGlu GlyAlaIleSer
ATGTCCGGCCTGAACGACATCTTCGAGGCTCAGAAAATCGAATGGCACGAA GGCGCGATATCC (G₄S)₂ Spacer                                          TEV CLEAVAGE SITE
GlyGlyGlyGlySerGlyGlyGlyGlySerGlyGlyGlyGlySer Ala GluAsnLeuTyrPheGlnGly
GGCGGCGGCGGCAGCGGCGGCGGCGGCAGCGGCGGCGGCGGCAGC GCG GAGAACCTGTACTTCCAGGGC 6x His Tag              Protein C
SerSerAla HisHisHisHisHisHis GlySer GluAspGlnValAspProArgLeuIleAspGlyLys
AGCAGCGCT CATCACCATCACCATCAC GGGAGC GAAGATCAGGTAGATCCACGGTTAATCGATGGTAAG
```

Example 2

Expression and Purification of Bacterially Expressed Proteins

Figure 2:
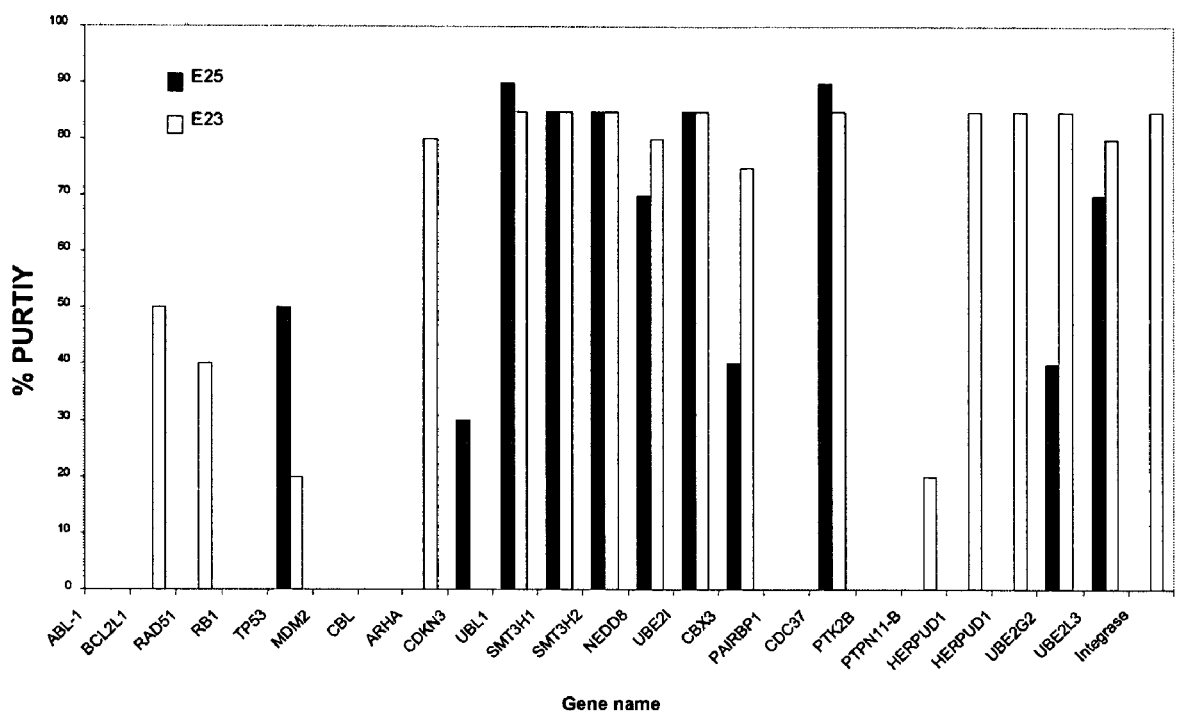
FIG. 2 shows that the E23- and E25-tagged fusion proteins expressed in E. coli can be purified significantly with only one step of affinity purification on Ni-NTA resin.

The E23, E24, and E25 constructs containing tag only (control with no bait protein) or various bait proteins such as Grb2, NAPA, CDKNb1 were expressed in *E. coli*. see FIGS. 1 and 2 for additional bait proteins.

In order to express the bait proteins, two ml of LB medium containing 100 µg/ml Ampicillin was inoculated with a single colony containing the desired expression vector and the culture was incubated at 37° C. in a shaker incubator. After 8 hours, one ml of the culture was diluted into 25 ml of fresh LB medium (100 µg/ml Ampicillin) and incubated overnight at 37° C. The overnight culture was diluted into 1 liter of LB medium containing 100 µg/ml of Ampicillin and an antifoam agent, in a Nalgene centrifuge bottle, to a final $OD_{595}$ of 0.05. The bottle was left immersed in a water bath (Bactolift apparatus) at 30° C. with an airflow of 10 cc/min into the culture bottle. When the culture reached an optical density of 0.7-0.9 at 595 nm, arabinose was added to a final concentration of 0.2% (w/v). After 3 hours of induction, the cells were harvested by centrifugation at 5000 rpm for 8 minutes in a Beckman JLA 8.1000 rotor. The supernatant was removed from the pelleted cells and the wet weight of the cells was determined. The cell pellet was resuspended in a 3-fold volume (v/w) of the lysis buffer (10 mM sodium phosphate, 150 mM NaCl, pH 7.2) and stored frozen in 50 ml conical tubes. The frozen cells were thawed in a 37° C. water bath and lysed by sonication in the presence of lysozyme (5 ug/ml) using a Virsonic 600 sonicator (20 sec pulse, 10 sec pause for at least 9 minutes). The supernatant was separated from the lysate by centrifugation for 30 minutes at 46,000×g.

Example 3

Purification of Expressed Proteins on a $Ni^{2+}$ Column

In order to purify the expressed proteins in E23-, E24-, and E25-tagged vectors, a 24-well Whatman deep well plate (UNI-FILTER, 24 wells, 10 ml, Polypropylene, Whatman GFC, MBPP 25-30, VWR International, West Chester, Pa.) was placed on top of the Whatman vacuum manifold system, and each well was loaded with 2 ml of Ni-NTA resin (Invitrogen Corp.) and pre-equilibrated with binding buffer (50 mM $Na_2HPO_4$, 500 mM NaCl, 10 mM Imidazole, pH 8.0). Ten ml of the supernant (cell extract) was added to each well and a vacuum was applied slowly to filter away the cell extract without disrupting the binding of the tagged fusion protein to nickel. An additional 10 ml of the binding buffer was added to each well and then eluted under vacuum. After two more rounds of washing with the binding buffer, in the same manner, the fusion proteins were eluted with 5 ml of elution buffer (50 mM $Na_2HPO_4$, 500 mM NaCl, 400 mM Imidazole, pH 7.4). The eluted proteins were dialyzed in 1 L of TBS (Tris buffered saline, 20 mM Tris, pH 7.5, 150 mM sodium chloride) for 2 hrs. The concentration of the protein was determined at each step.

Example 4

In Vitro Biotinylation of Avitag Containing Proteins in Solution and Binding to Neutravidin Bead Approximately 150 µg of purified protein (either in E24 or E25 vector) was incubated for 30 minutes at 30° C. in a reaction mix containing an equimolar amount of Biotin and 21 µg of purified recombinant biotin ligase, the gene product of BirA (Avidity, Denver, Colo.), in a total volume of 300 µl. The composition of each reaction mix, for each specific protein can be found in table 1 below. Due to the low molecular weight of the tag only construct, a lower amount of protein was used to maintain the equimolar ratio with Biotin. After the biotinylation the 300 µl reaction mix was then incubated for 20 minutes with 100 µl ULTRALINK NEUTRAVIDIN™ beads (Pierce, Rockford, Ill.). The supernatant was removed and the beads were washed 3 times with TEV cleavage buffer (50 mM Tris/HCl, 0.5 mM EDTA, pH 8.0) plus 10% Glycerol and then stored overnight at 4° C.

Alternatively, recombinantly expressed AVITAG™ containing proteins can be biotinylated when bound to the Ni-NTA beads. In this procedure, E25-tagged bait bound to the Ni-NTA beads following affinity purification is biotinylated before it is eluted from the beads with Imidazole. The E25-tagged bait bound beads are washed 2 times with Wash Buffer (50 mM $Na_2HPO_4$, 300 mM NaCl, 20 mM Imidazole, pH 8.0) and one time with 20 mM Tris buffer pH 7.5. The washed beads are then incubated in 50 mM bicine, pH 8.3, 10 mM MgOAc, 10 mM ATP with 1.5 µg birA enzyme per every 100 µl reaction volume. Biotin is then added at up to three times the molar amount of E25-tagged bait. The biotinylation reaction is allowed to proceed at room temperature for 30 minutes after which the beads are washed 3 times with Wash Buffer. The biotinylated bait is then eluted from the beads with Elution Buffer (50 mM $Na_2\ HPO_4$, 300 mM NaCl, 400 mM Imidazole, pH 8.0). The bait is then dialyzed against 150 mM NaCl, 20 mM Tris, pH 7.5, 50% glycerol and stored at −20° C. Alternately, the bait immediately after elution can be bound to TETRALINK™ beads, or a suitable avidin-like matrix, washed, and stored bound to the beads in 50% glycerol at −20° C. The biotinylation of bait on the Ni-NTA beads allows for the use of excess biotin in the biotinylation step which improves the yield of biotinylated bait and enables the removal of free biotin from the sample without the lengthy and sometimes detrimental dialysis step that would be required if excess biotin were used when biotinylating in solution. Removal of excess biotin is necessary since it competes with the bait for binding sites on the TETRALINK™ or other suitable avidin-like matrix, in preparation for pull-down reactions.

The degree of biotinylation and the efficiency of binding of the biotinylated proteins to the NEUTRAVIDIN™ beads was determined using a Western blot in which the proteins were visualized using a streptavidin-HRP conjugate (ZYMED Laboratories, San Francisco, Calif.) (see FIG. 3). Analyses were performed on the baits before and after biotinylation, as well as, on the supernatant after binding of the biotinylated baits to the beads. Approximately 40 ng of protein (both biotinylated and unbiotinylated) and 80 ng of supernatant were used for each analysis.

Figure 3B:
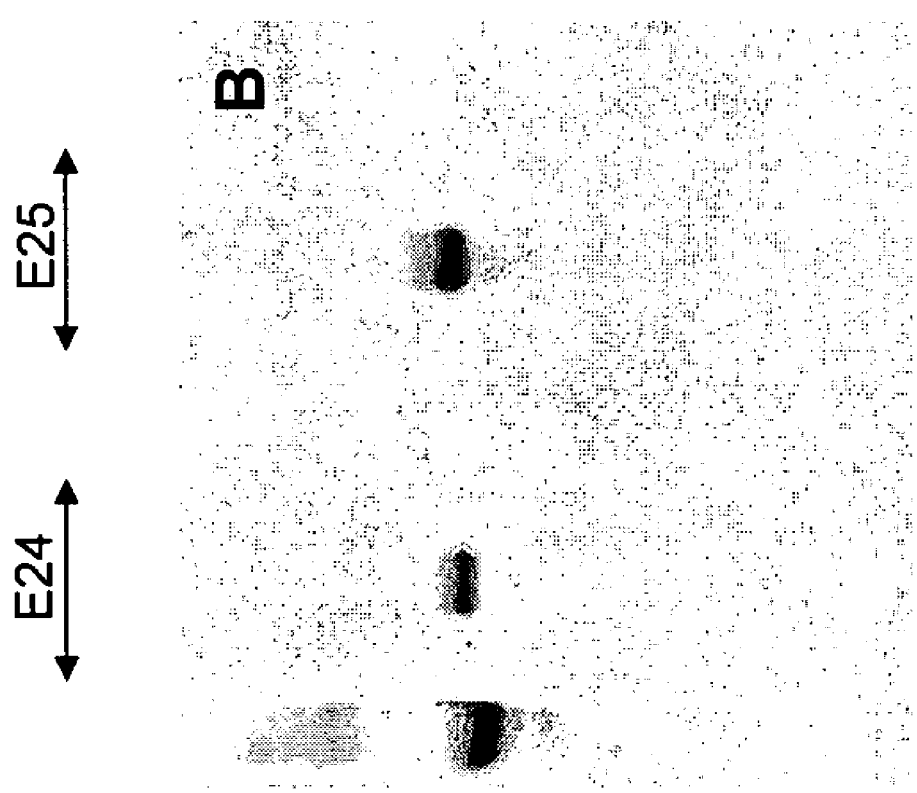
FIGS. 3A-3E confirm the biotinylation of the E24- and E25-tagged proteins and their ability to bind to neutravidin beads. Western blots are shown of samples [tags only (A), GRB2 (B), NAPA (C), CDKN1b (D)] taken before biotinylation, N, after biotinylation, B and the supernatant, S, following the binding to ULTRALINK NEUTRAVIDIN™ beads (Pierce, Rockford, Ill.) PS indicates the Mark12 Protein standards (Invitrogen, Calsbad, Calif.). Aliquots of approximately 20 ng of each purified protein sample were loaded on the gel. The Western blots were developed using NEUTRAVIDIN™—horseradish peroxidase complex and TMB (tetramethyl benzidine, Sigma, St. Lois, Mo.) substrate. Also shown in (E) is a gel-shift assay for the CDKN1 b-E25 fusion protein. Approximately 2 µg of expressed protein, before biotinylation, N, or after biotinylation, B, were incubated in the presence or absence of 4 µg of NEUTRAVIDIN™ protein, NA, and then analyzed by SDS-PAGE under non-denaturing conditions (nonreducing, unboiled).
Figure 3A:
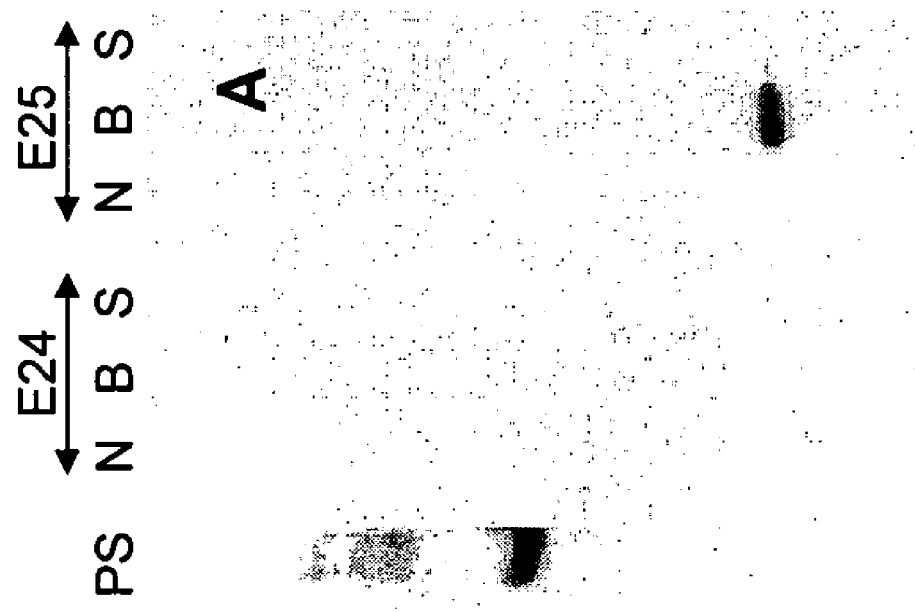
Figures 3C, 3D, 3E:
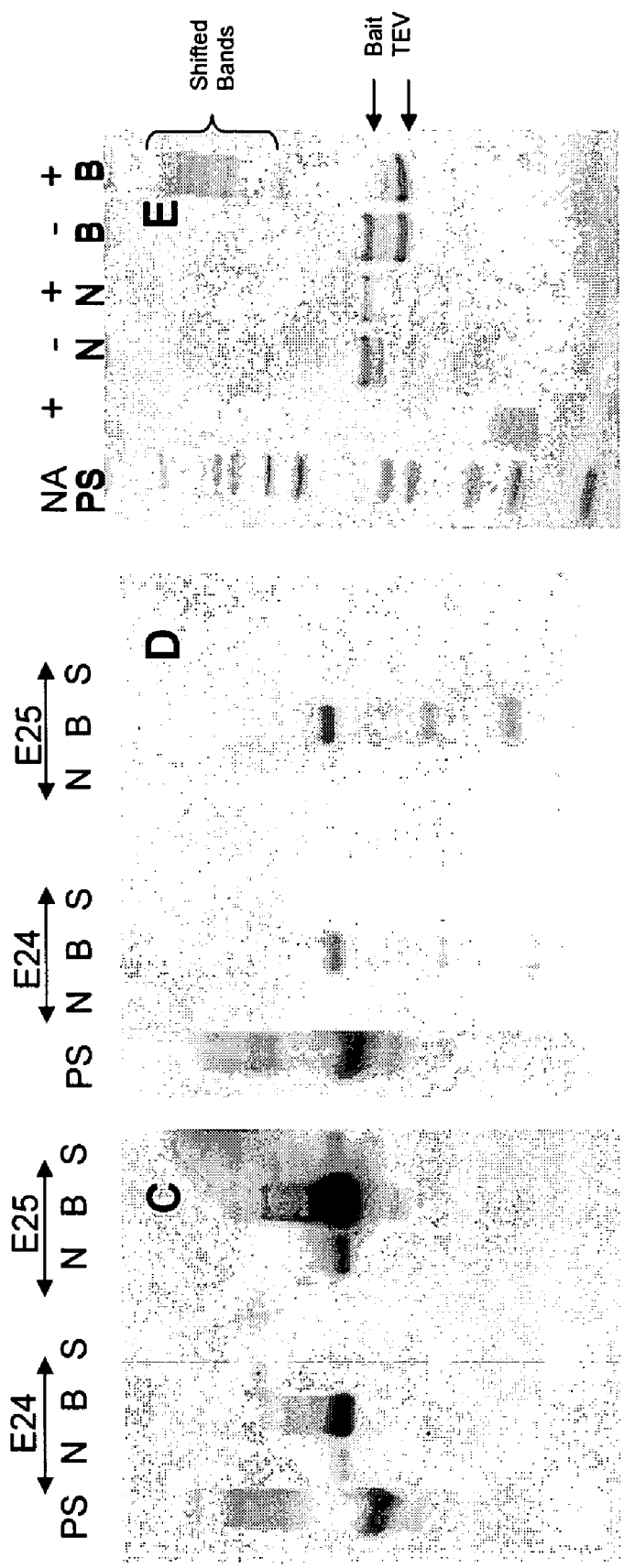
Figures 5A, 5B:
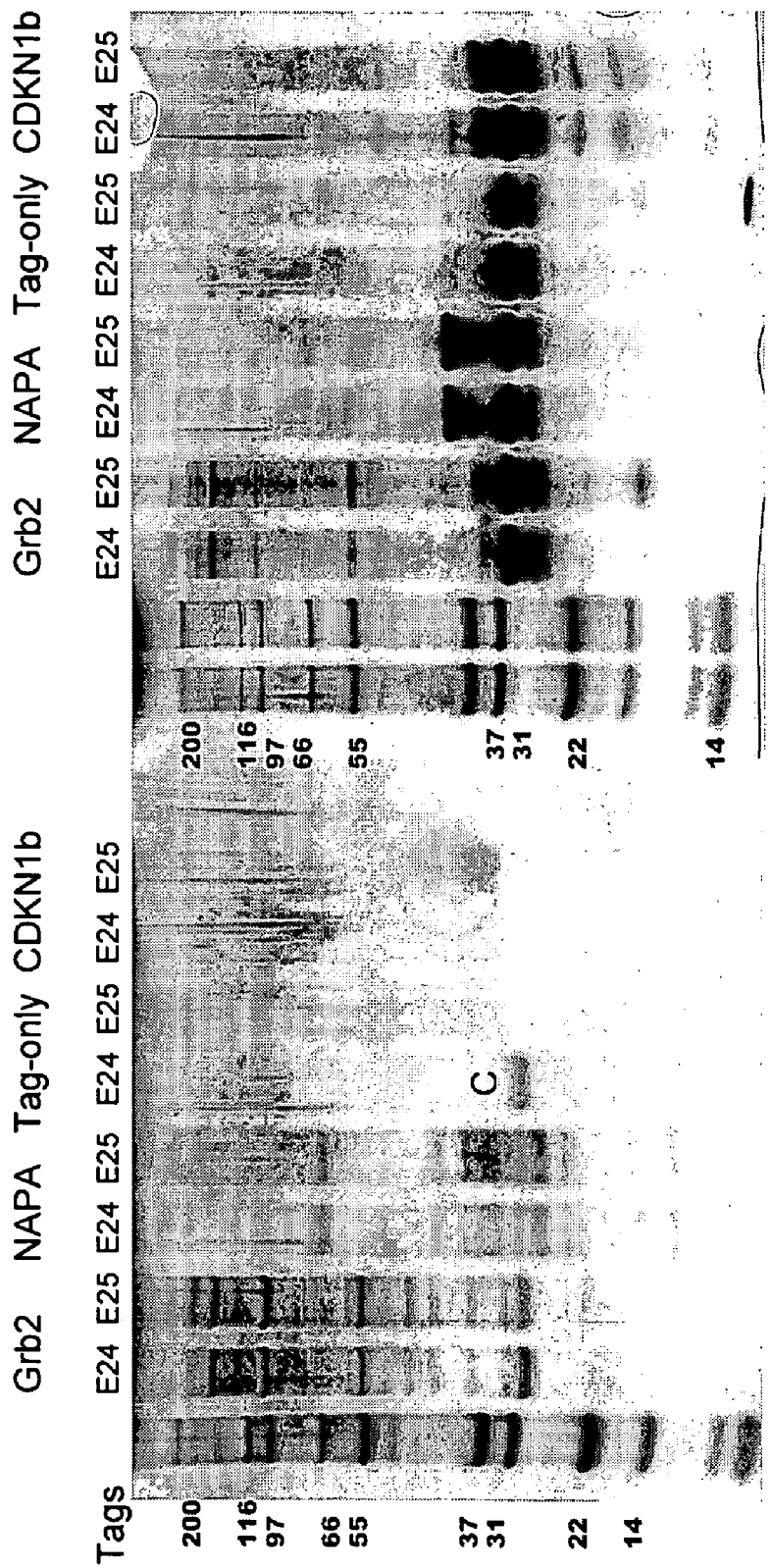
FIGS. 5A and 5B show the results of SDS-PAGE analysis of the isolated protein complexes following two-step affinity purification. Shown are proteins either eluted from the second affinity matrix ($Ni^{2+}$ beads) by a sarkosyl detergent or remaining on the beads following elution ($Ni^{2+}$ beads). The "C" label indicates contamination, due to bead carry-over, of TEV protease, which also contains a $His_6$ tag.
Figure 6:
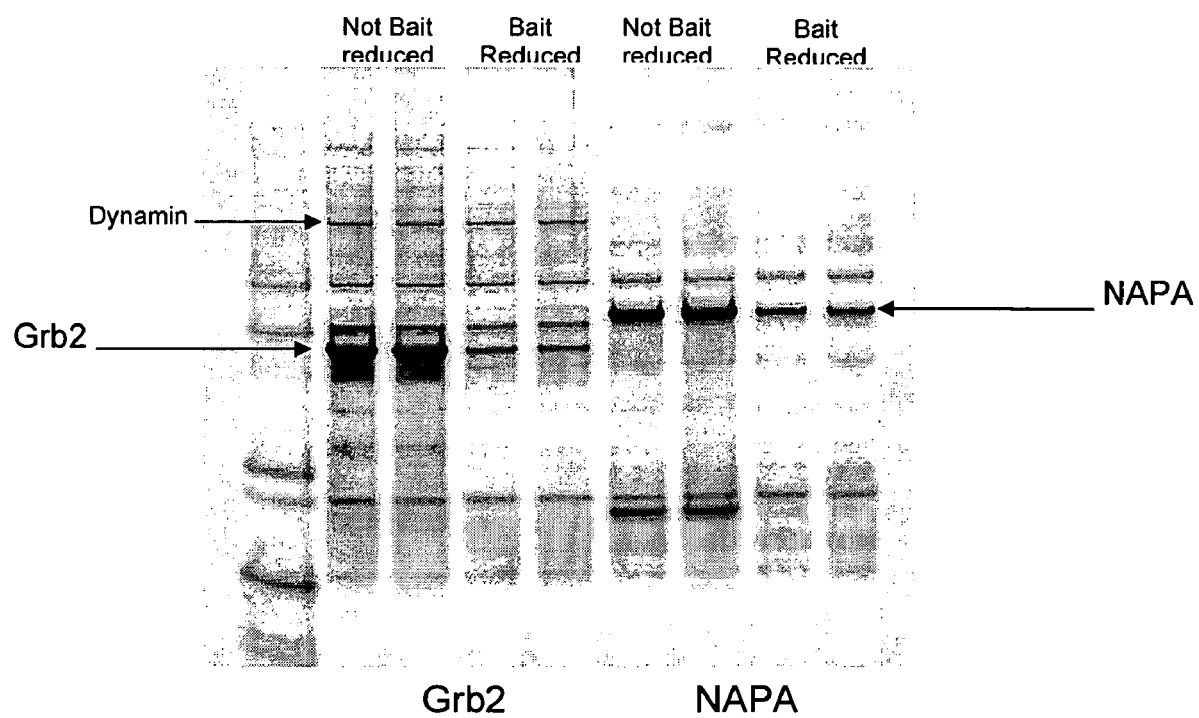
FIG. 6. illustrates the extent of the bait reduction in two E23-tagged fusion proteins, Grb2 and NAPA. Four pull-downs for each modified bait (Grb2 and NAPA) were performed as described in the Examples section and the interacting partner proteins were eluted by N-lauroylsarcosine (sarcosyl). The eluates for each modified bait were combined and divided into two equal parts; one part was bound to Ni-NTA beads to remove excess bait while the other remained as a control ("unreduced"). The samples (5 μl of each), reduced and unreduced, were analyzed on a gel. The results shown in FIG. 3 clearly demonstrate that the inclusion of one affinity step using Ni-NTA beads yields significant and specific reduction of the excess bait without significant loss of interacting proteins, as exemplified by Dynamin, a known interacting protein of Grb2.
Figure 7A:
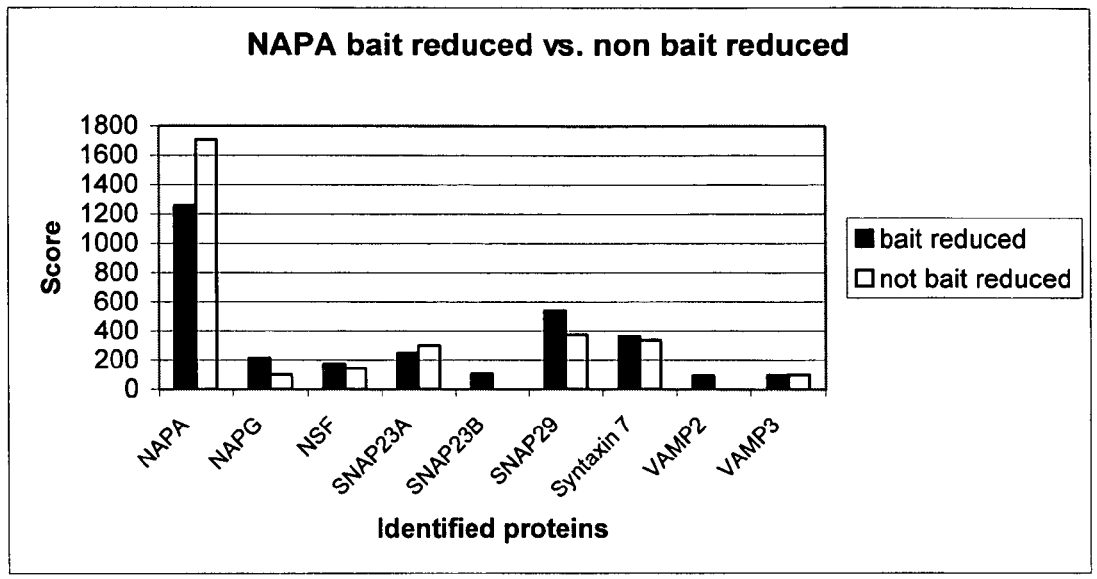
FIGS. 7A and 7B show the effect of bait reduction on the mass spectrometric identification of protein complexes with the samples generated from two E23 constructs containing either Grb2 (bottom) or NAPA (top) as bait. The E23-tagged fusion proteins were expressed and purified by glutathione affinity chromatography as described in the Examples section. The purified proteins were then used as bait in the pull-down assays with human cell lysate (HEK-293). In the case of the "not bait reduced" samples the proteins interacting with the immobilized bait were eluted with 0.8% N-lauroylsarcosine (sarcosyl) which disrupts any non-covalent protein-protein interaction. In the bait reduced samples the sarcosyl eluates were incubated with Ni-NTA beads to remove excess bait.
Figure 7B:
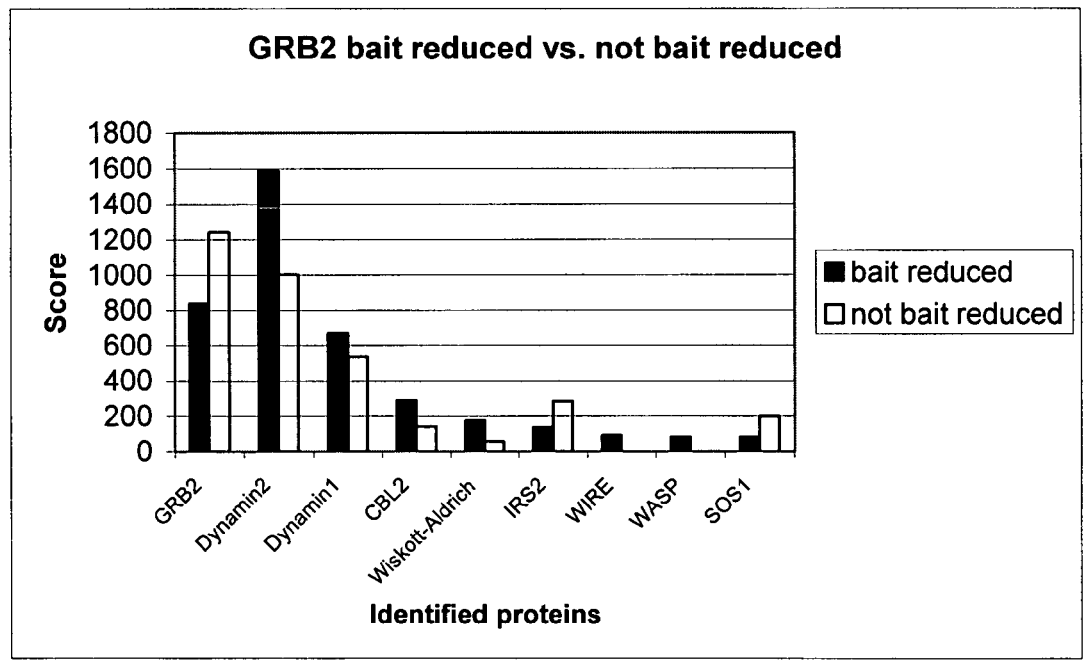

As can be seen in Table 2 and FIG. 3, in general, the proteins expressed in the vector E25 were biotinylated more efficiently than those expressed in the E24 vector. The binding of the protein to the beads was found to be in excess of 80%.

mM EDTA, 10% Glycerol, 0.1% NP-40, 1 mM DTT) and incubated with and without 310 μl of Hela cell lysate (5 mg/ml) prepared as described below, at 4° C. for 1 hr. The incubation mixtures were then washed 3 times with 1 ml HEGNS buffer and subjected to the TEV protease digestion step by adding 30 μl of HEGNS buffer containing 0.5 units or 5 units of TEV Protease (InVitrogen Corporation) per μg of the protein, and incubating at 4° C. for 1 hr. As a control, the uncleaved proteins were eluted with 50% Acetonitrile, containing 0.1% TFA, prior to the digestion step.

As shown in FIG. 4 in general, TEV protease digestion was efficient but varied depending on the specific bait protein. The presence of cell lysate under conditions that allow the formation of protein complexes with the first binding component bound to the beads did not affect the efficiency of proteolytic cleavage. Our experience with other TAP systems involving larger fusion tags indicates that this insensitivity of digestion to the presence of the formed complex is a major advantage of this particular tag design.

TABLE 1

Composition of reaction mixtures for in vitro biotinylation of bacterially expressed first binding components in the E24 and E25 vectors.

BirA 1.25 μg/μl Stock Biotin = 500 μM

|  | μg BirA | μl BirA | Water [μl] | Biomix B-Biotin [μl] | Biotin[μl] | Biomix A [μl] | Protein [μl] | Protein [μg] | Total Volume [μl] |
|---|---|---|---|---|---|---|---|---|---|
| E24-Tag-only | 21 | 17 | 193.4 | 30 | 9.6 | 30 | 20.0 | 30 | 300 |
| E24-GRB2 | 21 | 17 | 171.5 | 30 | 8.7 | 30 | 42.8 | 150 | 300 |
| E24-NAPA | 21 | 17 | 157.9 | 30 | 7.4 | 30 | 57.7 | 150 | 300 |
| E24-CDKN1b | 21 | 17 | 62.7 | 30 | 10.3 | 30 | 150.0 | 150 | 300 |
| E25-Tag-only | 21 | 17 | 201.4 | 30 | 9.6 | 30 | 12.0 | 30 | 300 |
| E25-GRB2 | 21 | 17 | 178.6 | 30 | 8.7 | 30 | 35.7 | 150 | 300 |
| E25-NAPA | 21 | 17 | 179.0 | 30 | 7.4 | 30 | 36.6 | 150 | 300 |
| E25-CDKN1b | 21 | 17 | 112.7 | 30 | 10.3 | 30 | 100.0 | 150 | 300 |

Biomix A: 0.5 M bicine buffer, pH 8.3
Biomix B: 100 mM ATP, 100 mM MgOAc

TABLE 2

Efficiency of the in vitro biotinylation and the binding of biotinylated E24, E25 tag-containing proteins evaluated by an ELIFA assay.

| | E24 tag | | | | E25 tag | | | |
|---|---|---|---|---|---|---|---|---|
| Sample | tag-only | Grb2 | NAPA | CDKN1b | tag-only | Grb2 | NAPA | CDKN1b |
| Biotinylation [%] | NA | 32 | 19 | 6 | NA | 50 | 82 | 23 |
| Binding [%] | NA | 100 | 100 | 100 | NA | 100 | 100 | 100 |

The results for % biotinylation are reported relative to the total protein in the sample. From the gel-shift assay performed with CDKN1b at least 80 to 90% of the specific CDKN1b band shifted indicating that % biotinylation for the pure protein is often higher than the results reported by the ELIFA.

Example 5

TEV Protease Digestion

Approximately 5 μg of each biotinylated bait protein, captured on the neutravidin beads, was washed with pull-down buffer, (HEGNS; 150 mM NaCl, 20 mM HEPES, pH 7.5, 0.1

Example 6

Purification of $His_6$-Tagged Proteins

The following describes the high-throughput purification of E23-tagged proteins in 24-well Whatman deep-well filter-plates. The binding to Glutathione (GSH) beads is necessary for the actual pull-down procedure to purify a protein complex.

A: Ni-NTA Affinity Purification

The following describes the purification of the E23-tagged fusion proteins using the $His_6$ tag.

Buffers:
  Binding Buffer: 50 mM $Na_2HPO_4$, 500 mM NaCl, 10 mM Imidazole, pH 8.0.
  Wash Buffer: 50 mM $Na_2HPO_4$, 500 mM NaCl, 20 mM Imidazole, pH 8.0.
  Elution Buffer: 50 mM $Na_2HPO_4$, 500 mM NaCl, 250 mM Imidazole, pH 8.0

Protocol:
  1. Place a 24-well, Whatman deep well filter plate on top of a Whatman vacuum manifold and seal all unused wells of the plate with aluminum sealing tape.
  2. Add 2 ml of Ni-NTA resin (Invitrogen) into each unfilled well of the filterplate and equilibrate the resin with 10 ml of binding buffer under slow acuum flow.
  3. Add 10 ml of crude cell lysate containing the expressed fusion protein (the cell lysate can be obtained from the recombinant host cells and can be from bacterial, mammalian or insect cells for example) into each well of the filterplate and withdraw the lysate through the filter very slowly (ca. 30 min) with a low acuum, to ensure optimal binding of the tagged fusion protein to the Ni-NTA resin.
  4. Wash the resin three times with 10 ml of washing buffer in each well and allow the buffer to pass through the filter using maximum vacuum.
  5. Elute the bound protein by washing twice with 2 ml of elution buffer into a fresh 24-well collection plate.
  6. The purified proteins are dialyzed against TBS (20 mM Tris/HCl, 150 mM NaCl, pH 8.0) for 2 hrs at 4° C.
  7. The protein concentration of the purified proteins is determined by a Bradford assay.
  8. The proteins are then, if necessary, subjected to a second purification step by GSH affinity chromatography as described in section B or stored either in solution at –20 C. in 50% Glycerol or bound to GSH beads as described in section C.

B: GSH-Affinity Purification

Alternatively, the E23-tagged fusion proteins can be purified via GSH-affinity chromatography which is described below.

Buffers:

Binding buffer: PBS, pH 7.2(Invitrogen, cat# 20012-027), 1 mM DTT, 0.05% NP-40.

Wash buffer: Binding buffer+0.5M NaCl

Elution buffer: 20 mM Tris-HCl, pH 8.0, 10 mM reduced glutathione, 5 mM DTT (check the pH before application).

Protocol:
  1. Place a 24-well Whatman deep well filter plate on top of a Whatman vacuum manifold and seal all unused wells with aluminum sealing tape.
  2. Transfer an appropriate amount of GSH beads (capacity ca. 10 mg protein per ml gel) into each unfilled well of the plate.
  3. Equilibrate the beads with 10 ml of Binding Buffer.
  4. Add 10 ml of crude cell lysate containing the expressed fusion protein into each well of the filterplate and draw the lysate through the filter very slowly (ca. to the GSH beads.
  5. Wash the beads by adding 10 ml of binding buffer to each well and allowing the buffer to pass through the well under the influence of the vacuum.
  6. Wash the beads with 10 ml of wash buffer.
  7. Wash the beads with 10 ml of 20 mM Tris-HCl, pH 7.5.
  8. Elute the GST-tagged protein by using 2 washes with 2 ml of 10 mM Glutathione in pH 8.0 20 mM Tris into a fresh 24-well collection plate.
  9. The purified proteins are then dialyzed against TBS for 2 hrs and the protein concentration is determined by a Bradford assay.
  10. The proteins are either stored at –20° C. in 50% Glycerol or subjected to a second purification by Ni-NTA affinity chromatography as described in Section A.

C: Storage of Ni-NTA Purified Proteins on GSH Beads

Buffers:

Binding Buffer: PBS w/1 mM DTT, 0.05% NP-40

Wash Buffer II: PBS containing 500 mM NaCl

Wash Buffer III: 20 mM Tris-HCl, pH 7.5.

Protocol:
  1. Prewash GSH beads 3 times with binding buffer.
  2. Incubate each protein eluate (in 15 ml centrifuge tubes) from the Ni-NTA purification with the appropriate amount of GSH beads (ratio: use 1 ml of bead volume/3 µg protein) at 4° C. while continuously rotating the tube for 30 minutes.
  3. Wash the beads 2× with 5 ml of wash buffer II. Change the tube after the first wash.
  4. Wash the beads with 10 ml of wash buffer III.
  5. Centrifuge briefly and remove the supernatant, add equal volumes of TBS containing 50% glycerol, 5 mM DTT, store at –20° C.

Example 7

Protocol for Protein Complex Purification using E23-Tagged Baits ("Pull-Down Assay")

One ml of 5 mg/ml HeLa whole cell lysate prepared as described below was incubated for 1.5 hrs rotating at 4° C. with 1 µl bed of GSH beads (Amersham Pharmacia-Biotech) bound to 30 µg E23-tagged bait protein. The incubation vessel was rotated during the incubation. After incubation, the samples were briefly centrifuged to pellet the beads and the lysate removed. The beads were transferred to clean Eppendorf tubes and washed three times with 1 ml of pull-down buffer (20 mM HEPES, pH 7.5, 150 mM NaCl, 10% glycerol, 0.1% NP-40). Bound complexes were eluted in three fractions of 75, 75, and 100 µl of pull-down buffer containing 0.2% N-lauroylsarcosine and the eluates were combined. The eluates were then spiked with 10 mM Imidazol and incubated with a 10 µl bed of Ni-NTA agarose (InVitrogen) for 30 min at 4° C., to reduce the amount of bait in the sample. The supernatant from the nickel beads was removed and 5 µl of each sample was analyzed by SDS PAGE while the remainder was precipitated with ethanol prior to mass spectrometric analysis.

Example 8

Protocol for Protein Complex Purification using E24- or E25-Tagged Baits ("Pull-Down Assay")

One ml of HeLa cell lysate (5 mg/ml) was incubated at 4° C., for 1.5 hrs, with 15 µl of streptavidin beads, containing 5 µg of each of the first binding components. The samples were briefly centrifuged to pellet the beads after which the lysate was removed. Beads were transferred to clean eppendorf tubes and washed three times with 1 ml of pull-down HEGNS buffer (20 mM HEPES, pH 7.5, 150 mM NaCl, 10% glycerol, 0.1% NP-40). Protein complexes were released from the beads by incubating the bead bound complexes with 100 µl of pull-down buffer, containing 50 units of TEV protease and incubation for 1 hr at 4° C. while rotating the container. After incubation the supernatant was removed. An additional 50 µl of pull-down buffer was added to the beads, gently mixed. The supernatant was subsequently removed and combined with the previous supernatant. Imidazole, to a final concentration of 10 mM, was added to the combined supernatant. The resultant solution was then incubated with a 10 µl volume of nickel equilibrated Chelating-NTA SEPHAROSE™ agarose beads (Amersham Biosciences, Piscataway, N.J.) beads at 4° C. for 30 min. The supernatant was removed from the nickel beads, after which the beads were washed three times with pull-down buffer, containing 10 mM imidazole. Proteins associated with the bait were eluted in three fractions of 50 µl of pull-down buffer containing 0.8%(w/v) N-lauroylsarcosine and the eluates were combined. 1 µl of each sample was analyzed by SDS PAGE and the remainder was precipitated with ethanol in preparation for mass spectrometric analysis.

Example 9

Mammalian Whole Cell Lysate Preparation

To provide a source of mammalian proteins to interact (in pull-down analyses) with purified mammalian bait proteins expressed in bacteria or another host organism, large scale cultures of mammalian cells (2-25 liters) were grown in suspension to densities of $2-5 \times 10^6$/ml or ~80-90% confluency for adherent cultures. Once the suspension cultures reached their desired density, the cells were centrifuged at 3,000×g for 10 minutes. The resulting cell pellet (or plate of adherent cells) was washed 1× with cold phosphate buffered saline (PBS). The PBS was removed and cold lysis buffer was added at a volume of 10 µl per mg of wet cell weight or 1 ml per 15 cm plate of adherent cells. The lysis buffer consists of 25 mM N-(2-ydroxyethyl)piperazine-N'-2-ethanesulfonic acid (HEPES) pH 7.5, 150 mM NaCl, 1% NP40, 10 mM $MgCl_2$, 1 mM ethylene-diamine tetra acetate (EDTA), 10% Glycerol, 1 mM dithiothreitol (DTT), and a protease inhibitor cocktail (Roche, Mannheim Germany) added just prior to application (1 tablet/10 ml of buffer). Once the lysis buffer was added, the suspension cell pellet was resuspended with gentle pipetting and slow speed vortexing. The adherent cells were lysed (on ice) by adding the buffer directly to the culture plate and scraping the cells off of the dish. The lysates were then transferred to centrifuge tubes and allowed to incubate at 4° C. for 15 minutes. At 2 minute intervals during the 4° C. incubation, the lysates were gently resuspended with mild shaking and/or slow speed vortexing. Following the incubation, the lysates were centrifuged at 27,000×g for 15 minutes at 4° C. to remove insoluble debris. The supernatant was then aliquoted into fresh centrifuge tubes, snap frozen in liquid nitrogen and then stored at −80° C.

As quality control measures to assess the abundance and functionality of the proteins within the whole cell lysates we first determined the protein concentration using a Bradford colorimetric assay from Bio-Rad (Hercules, Calif.). Once the concentration of the lysate preparation was established, we tested the lysates with one or more of the following assays:
  a. histone deacetylase (HDAC) activity assay to assess nuclear protein activity;
  b. alkaline phosphatase assay to assess cytoplasmic protein function;
  c. western blots for expression of specific proteins of interest such as but not limited to HDAC.

Once found to perform satisfactorily in the above assays, the lysate is then made available for use in downstream analyses such as pull-down interaction studies.

In attempts to identify a whole cell lysis protocol which provided sufficient quantities (and concentrations) of biologically active proteins to serve as interactors in pull-down studies, we tested nine separate protocols derived from commercial sources or culled from journal articles. The protocols and the resulting lysates, were initially evaluated using four primary criteria: total protein yield per mg of wet cell weight, protein purity as assessed by refractive index and optical density measurements at A260, A280 and A600, biological activity of proteins of the nuclear compartment as assessed by histone deacetylase activity and the biological activity of proteins of the cytoplasmic compartment as assessed by alkaline phosphatase activity. Five of the nine protocols were discarded due to either poor protein yields, poor biological activity or because they utilized detergents or compounds which were found to be detrimental to or incompatible with our downstream mass spectrometry processes. The remaining four frontrunners from the aforementioned evaluations were further examined using our most stringent test; mass spectrometric analysis of a pull-down. The mass spectrometry data was carefully analyzed to determine which buffer/protocol facilitated the identification of the largest number of curated and novel interacting proteins, the highest strength or quality of protein identifications and the fewest non-specific interactions or cleanliness of the data.

As a result of these experiments, a buffer and protocol that we developed clearly outperformed all others. The protocol was modified from that described by De Rooij and Bos [Oncogene (1997) 14:623-625]. Modifications of the published protocol include the addition of 1 mM dithiothreitol, which mimics the reducing environment that normally exists inside mammalian cells and the increase of the force of centrifugation from 18,000×g to 27,000×g to remove excess debris. These modifications were made to maintain protein stability and reduce nonspecific binding, respectively, thereby improving downstream mass spectrometry results. In summary, we have found that this protocol maximizes the yield of total protein per mg of wet cell weight, the biological activity of the resulting proteins and the identification of protein-protein interactions by mass spectrometry. To our knowledge, neither the original nor the modified protocol have been used for the mass spectrometry analysis of protein-protein interactions. It was this reagent that was used to generate the data put forth in this application.

Example 10

Tissue Lysate Preparation

Tissues used to date include whole mouse brain and mouse cerebellum. Modification to the following protocol for different organs can easily be made by those skilled in the art. For example, those skilled in the art will understand that more aggressive tissue disruption for muscle tissue than for brain is required because of the larger amount of connective tissue. Tissues were flash frozen in liquid nitrogen immediately following dissection. Frozen brain or cerebella were weighed. Mouse cerebella weighed approximately 70 mg, the striatum was approximately 30 mg and the cortex was about 80 mg. Tissues were then mixed with cold homogenization buffer of 25 mM hydroxyethylpiperazine-N'-2-ethanesulfonic acid (HEPES) pH 7.5, 150 mM NaCl, 1% NP40, 10 mM $MgCl_2$, 1 mM ethylene-diamine tetra acetate (EDTA), 10% Glycerol, 1 mM dithiothreitol (DTT), and a protease inhibitor cocktail (Roche, Mannheim Germany) at a ratio of 100 mg tissue to 1 ml of buffer. The tissue was then homogenized on ice with a Dounce homogenizer (Wheaton brand) for 5 plunges with a loose pestle and 25 plunges with a tight pestle. The resulting brain tissue homogenate was then centrifuged at 100,000×g for 30 minutes. The resulting supernatant was used for pull-down assays according to the protocol for cell lysates. 100 mg of brain tissue typically yields approximately 10 mg of protein lysate.

Example 11

Expression of the First Binding Component Containing AVITAG™ in Mammalian Cells

The mammalian expression vectors used herein are referred to as M08-TAG and M09-TAG and contain the nucleotide sequences capable of expressing a fusion protein of the following general design:

AVITAG™-(+/−spacer)-(TEV protease site)-(+/−spacer)-His$_6$ tag-(+/−spacer)-(+/−PRESCISSION™ cleavage site)-(+/−Protein C tag)-(bait protein).

A total of six genes (PCNA, HDAC, CDKN1b, NAPA, CDK5, Tag-only) were expressed from three separate vectors designated as M07, M08, and M09, which encoded three variations of an N-terminal tag (see below for details) designed for tandem affinity purification. The base vector was derived from an expression plasmid, pT-Rex-DEST30 purchased from Invitrogen Corporation (Carlsbad, Calif.). In pT-Rex-DEST30, gene expression is driven by the cytomegalovirus (CMV) immediate early promoter under the control of the tet operator sequence fused to the 3' end of the promoter.

The M07 and M08 vectors are similar in that the functional elements of the tag sequences are identical with the exception that the M08 vector encodes a triple unit repeat of four glycine residues and one serine residue to serve as a spacer to permit more efficient cleavage of bait proteins from the purification tags.

The M09 vector is similar to the M07 construct in that it does not contain the triplet repeat spacer, but diverges from the M07 vector due to the substitution of a Protein C binding domain in place of the PRESCISSION™ protease cleavage site. This design relies on the efficiency of the TEV protease for the removal of the bulk of the tag and affords additional flexibility for purification by incorporating the high affinity Protein C domain. The annotated nucleotide sequences (from the start of the ORF to the beginning of the bait protein) are as follows:

M07-TAG (SEQ ID NOs: 26 and 27)

```
AVITAG ™ SEQUENCE
MetSerGlyLeuAsnAspIlePheGluAlaGlnLysIleGluTrpHisGlu GlyAlaIleSerAla
ATGTCCGGCCTGAACGACATCTTCGAGGCTCAGAAAATCGAATGGCACGAA GGCGCGATATCCGCG

TEV CLEAVAGE SITE       SPACER      6X His Tag
GluAsnLeuTyrPheGlnGly  SerSer Ala  HisHisHisHisHisHis Val
GAGAACCTGTACTTCCAGGGC  AGCAGC GCT  CATCACCATCACCATCAC GTG

PRESCISSION ™ CLEAVAGE SITE BAIT SEQ
LeuGluValLeuPheGlnGlyPro XXXXXXX
CTGGAAGTTCTGTTCCAGGGGCCC NNNNNNN
```

M08-TAG (SEQ ID NOs: 28 and 29)

```
AVITAG ™ SEQUENCE
MetSerGlyLeuAsnAspIlePheGluAlaGlnLysIleGluTrpHisGlu GlyAlaIleSer
ATGTCCGGCCTGAACGACATCTTCGAGGCTCAGAAAATCGAATGGCACGAA GGCGCGATATCC

Gly₄-Ser Spacer
GlyGlyGlyGlySer GlyGlyGlyGlySer GlyGlyGlyGlySer Ala
GGCGGCGGCGGCAGC GGCGGCGGCGGCAGC GGCGGCGGCGGCAGC GCG TEV CLEAVAGE SITE       SPACER      6X His Tag
GluAsnLeuTyrPheGlnGly  SerSer Ala  HisHisHisHis
GAGAACCTGTACTTCCAGGGC  AGCAGC GCT  CATCACCATCAC PRESCISSION ™ cleavage site
HisHis Val  LeuGluValLeuPheGlnGlyPro
CATCAC GTG  CTGGAAGTTCTGTTCCAGGGGCCC
```

M09-TAG (SEQ ID NOs: 30 and 31)

```
AVITAG ™ sequence
MetSerGlyLeuAsnAspIlePheGluAlaGlnLysIleGluTrpHisGlu GlyAlaIleSerAla
ATGTCCGGCCTGAACGACATCTTCGAGGCTCAGAAAATCGAATGGCACGAA GGCGCGATATCCGCG TEV cleavage site     spacer    6X His Tag
GluAsnLeuTyrPheGlnGlySerSerAlaHisHisHisHisHisHis
AGCAGCGCTCATCACCATCACCATCACGAGAACCTGTACTTCCAGGGC Protein C
GlySerGluAspGlnValAspProArgLeuIleAspGlyLys
GGGAGCGAAGATCAGGTAGATCCACGGTTAATCGATGGTAAG
```

The tag configuration of the mammalian vectors was as follows:

M01 AT-ek-FLAG

M07 AT-TEV-HIS-PS

M08 AT-(G$_4$S)$_3$-TEV-HIS-PS.

M09 AT-TEV-HIS-PrC

Where

AT=AVITAG™ (Avidity, Denver, Colo.)

FLAG=FLAG epitope

TEV=Tobacco Etch Virus (TEV) protease cleavage site ek=enterokinase cleavage site HIS=6× Histidine tag PrC=Protein C epitope Tag PS=PRESCISSION™ Protease Cleavage site (G$_4$S)$_n$=spacer region containing -Gly-Gly-Gly-Gly-Ser (SEQ ID NO: 32) with "n" repeats M01 was made by amplifying by PCR using the following primers

```
GGAACCGGTGAAGGAGATAGAACCATGTCCGGC    (SEQ ID NO: 33)
CTGAACGAC-PinAl-SD-Avi-F

TCCCTCGAGCCGTCGTCGTCATCCTTGTAGTC-    (SEQ ID NO: 34)
XhoI-FLAG-R
``` using vector pAN5rfc.1 FLAG as template. Vector pT-REx-Dest30 and PCR product were both digested with PinA1 and Xho I and ligated together.

M07 was created by inserting a DNA fragment encoding "TEV-Ser$_2$ spacer-6× HIS tag-PS cleavage site" and oligonucleotides encoding AscI, EcoRV, SacII restriction sites on the 5' end and XhoI site on the 3' end. Also included were an EcoR47III site between the Ser$_2$ spacer and 6× HIS tag and a PmlI site between the 6× HIS tag and the PS cleavage site. The "top and bottom strand" oligos were annealed and cut with AscI/XhoI and cloned into an AscI/XhoI-cut M01 vector. (The AscI site is not regenerated to avoid creating a Proline). Cloned sequences were verified by DNA sequencing.

M08 was created by inserting a DNA fragment encoding (G$_4$S)$_3$ and oligonucleotides with an EcoRV site at the 5' end and a SacII site at the 3'end. The "top and bottom strand" oligos were annealed and cut with EcoRV/SacII and cloned into an EcoRV/SacII-cut M07 (pMASH2) vector. (The SacII site is not regenerated). Cloned sequences were verified by DNA sequencing.

The mammalian expression vector M09 was made from the vector M07. The result of this construction was to introduce the coding sequence for the Protein C epitope tag and at the same time remove the PRESCISSION™ cleavage site.

Construction of M09 was achieved by amplifying the tag region of M07 with the following oligonucleotide primers in a polymerase chain reaction (PCR). MACH.Forward—(purchased from MWG, High Point, N.C.)

```
5'-GACGAGCTCGTTTAGTGAACCGTCAGATCGC    (SEQ ID NO: 35)
CTGGAGACGCC-3'
```

This primer binds to a region 129 bp upstream of the AVITAG™ coding region.

MACH. Reverse

```
5'CATGACGAGCTAGCTAGCCTCGAGCTTACCAT    (SEQ ID NO: 36)
CGATTAACCGTGGATCTACCTGATCTTCGCTCCC
GTGATGGTGATGGTGATGAGCGCTGCTGCC-3'
```

This primer encodes the Protein C epitope tag region at the 5' end and the 3' region binds to the His$_6$ region as indicated in the design above. The primer also encodes an Xho I site directly after the Protein C tag. Using these two primers with M07 as the PCR template, the sequences were amplified and the resultant PCR amplicon was digested with PinAI (restriction site is 15 bp upstream of the Avitag ATG codon) and Xho I (site is with MACH.Reverse) and sub-cloned into PinAI/XhoI digested vector backbone M01 and transformed into DB3.1 bacterial cells. Positive colonies were identified and verified by DNA sequencing. The result of this procedure was the replacement of the PS region with the Protein C region.

Transfection

Each plasmid was transfected into 293 T-Rex cells (Invitrogen Corporation, Carlsbad, Calif.) using the following protocol: 24 hours prior to transfection, cells were plated at 90% density in 10 cm tissue culture plates. For DNA complex formation and transfection, 24 ug M07, M08 or M09 plasmid DNA containing the nucleotide sequence encoding one of the six bait proteins as listed above, was diluted in 1.5 ml of serum free media. 60 µl Lipofectamine 2000 reagent (Invitrogen Corp. Carlsbad, Calif.) was diluted in 1.5 ml serum free media. After a five minute incubation period at room temperature, the DNA and transfection reagent dilutions were combined, mixed gently and allowed to incubate for 20 minutes at room temperature. The Lipofectamine/DNA mixture was then added to the media of 293 T-Rex cells at ~90% density in 10 cm plate, rocked gently and placed in an incubator at 37° C. (5% CO$_2$). Following a 4 hour incubation period, the media were changed and the cells were placed back in the incubator. 24 hours after the transfection, 250 µg/ml of geneticin antibiotic was added to the culture media to eliminate non-transfected cells.

The 293 T-REX™ cells (Invitrogen Corp. Carlsbad, Calif.) are engineered to express the tet repressor protein, and thus protein expression from the M07, M08, M09 vectors is restricted in the absence of tetracycline. Addition of tetracycline displaces the tet repressor protein and allows transcription from the CMV promoter. Seven days after transfection and multiple passaging of the cell populations to permit sustained expansion, transgene expression was induced by adding tetracycline at a final concentration of 10 ug/ml for a period of 48 hours. Following the period of induction, the media were removed, the culture plates were rinsed once with cold phosphate buffered saline and protein lysates containing the first binding component expressed from vectors M07, M08 and M09 were harvested using a gentle lysis buffer as described in Example 12.

Example 12

Preparation of Cell Lysates from Mammalian Expression System

Harvested mammalian cells expressing the modified bait proteins are then lysed according to the procedure described above for whole cell lysates using our optimized protocol (see Example 9). If biotinylation of the modified bait protein has not occurred by co-transfection or the creation of stable cell lines expressing the biotin ligase (e.g. BirA) [Pyrrott MB & Barry Mass. (2001) BBRC 281, 993-1000: Pyrrott MB & Barry Mass., (2002) Mol Ther. 1: 96-104), biotinylation is performed using the cell lysate according to the protocol for purified recombinant modified bait protein, except that the biotin concentration is reduced. The amount of enzyme and biotin in the reaction can be adjusted according to the level of expression of the modified bait protein as determined by immunochemical assays specific to the second affinity tag segment. Concentrations of biotin as low as 10 to 20 nM can be used for efficient biotinylation and at these concentrations remaining free biotin does not interfere with subsequent binding to neutravidin beads. Cell lysate containing biotinylated bait and associated interacting proteins are then purified as described herein.

Example 13

Use of Transgenic Animals to Purify Protein Complexes

Transgenic animals provide enormous potential for the study of biological processes and the modeling of disease [Prosser, H and Rastan S., *Trends Biotechnol*. (2003) 21(5): 224-32]. Typically, they are generated by the introduction of recombinant DNA expression constructs into a very early stage embryo which matures to become an adult organism. This is accomplished by microinjecting the DNA into a single embryonic stem cell which is then implanted into a blastocyst or multicell embryo. The blastocyst is then implanted into a pseudo-pregnant female where, if all goes well, the embryo develops into a healthy newborn. The introduced DNA can be designed to either integrate randomly into the genome, integrate specifically in the genome and remove or replace existing sequences by homologous recombination as in a "knock-out" or integrate specifically to introduce sequences as in a "knock-in." Using existing technologies for the formation of transgenic animals, it would be possible to introduce the coding sequences for a tagged protein or proteins into intact, living organisms including but not limited to mice, rats, rabbits or primates. Using this approach, the experimentalist would essentially be able to perform an in vivo pull-down experiment. The primary advantages of this technique include: (1) the ability to provide all potential interacting proteins in the appropriate context; (2) the ability to analyze protein-protein interactions from each/any organ system independently; (3) the ability to examine protein-protein interactions over time and through every developmental stage of the host organism; and (4) the ability to combine the study of tagged protein-protein interactions with established animal models of acquired and inherited disease.

Refinements of this approach could include the utilization of naturally or artificially regulated and/or tissue specific promoters to induce or direct expression of the tagged protein at a specific time, dose or in a desired subset of organismal tissues [Chandrasekaran et al. (1996) *J. Biol. Chem*. 271(45): 28424-21]. This technique could be employed if a given protein were found to be toxic or, not well tolerated in a host animal or simply if the experimental design required specific expression levels or tissue restriction of expression.

Similarly, it should be possible to capitalize on the ability to perform a "knock-out" recombination reaction where an endogenous gene or genes could be replaced by a tagged wild type or mutant version of the same gene [Chandrasekaran et al. (1996) supra]. This would eliminate any potential effects or competition produced by the presence of the endogenous gene product and permit clearer analysis of the tagged protein behavior [Lees-Miller et al. (2003) *Mol. Cell Biol*. 23(6): 1856-1862]. A technically simpler variation of this approach, which would obviate the need for homologous recombination, would be to combine the use of a transgenic animal expressing a tagged molecule of interest with the use of a gene expression "knock-down" strategy such as, but not limited to, RNA interference (RNAi) or anti-sense thereby eliminating or reducing the influence of the native gene product [Forler et al. (2003) *Nat. Biotechnol*. 21(1):89-92].

A further embodiment of this approach could include the use of "knock-in" homologous recombination to specifically insert the preferred tag sequences in frame, (N-terminally, C-terminally or internally) with a given gene such that the augmented gene sequence would encode the desired fusion peptide with minimal disruption of the native gene promoter/enhancer sequences [Yu et al. (2003) *Neurosci*. 23(6):2193-202].

Finally, once created, the transgenic animals could be interbred to facilitate studies of one or more biological pathways in which it might be advantageous to have multiple tagged proteins present in the living organism.

A tissue lysate can be prepared from a transgenic animal as described above and a protein complex can be purified and interactor proteins can be identified according to the invention disclosed herein.

Example 14

Mass Spectrometric Analyses for Protein Identification

Sample Digestion

Protein mixtures isolated from a pull-down assay described above were digested with trypsin in solution to produce a mixture of peptides. The procedure is as follows:

An approximately 10 ug protein pellet was dissolved in 10 µl of 50% aqueous acetonitrile (AcN)/0.1% trifluoracetic acid (TFA) solution to form a protein solution, and 50 µl of an 8M aqueous Urea/0.2M $NH_4HCO_3$ solution was added thereto. Next, 10 µl of 45 mM aqueous dithiothreitol (DTT) solution was added to the protein solution and the resulting solution was mixed with a vortex mixer and then incubated for approximately 15 minutes at 60° C. After cooling the protein solution to room temperature (about 5 minutes), 10 µl of a 100 mM iodoacetamide solution was added, and the resulting solution was then incubated at RT for approximately 15, minutes in the dark. The protein solution was diluted with 120 µl of purified water and 5 µl of 0.1 µg/µl Trypsin solution was added thereto. The resulting solution was incubated at 37° C. for approximately 2 hours. After allowing the digested protein solution to cool to RT, 10 µl of 10% TFA was added to quench the trypsin. The resulting solution was then concentrated, under vacuum, to yield a final volume of approximately 100 µl, in preparation for desalting.

CEX Fractionation of Digested Proteins

The digested proteins were desalted using a C-18 reverse phase cartridge (Michrom BioResources, Auburn Calif.) to remove the salt from the digestion buffer. They were eluted with 95% AcN in water which contains 0.1% TFA by volume. Afterwards the eluted sample was taken to dryness in a vacuum centrifuge and then reconstituted in 5 microliters of 2% aqueous AcN containing 0.5% aqueous acetic acid by volume. The reconstituted sample was then injected onto a 300 micron×5 cm strong cation exchange (CEX) column (Vydac column, Western Analytical Services, Marietta, Calif.) which was eluted using 250 mM NH₄OAc flowing at 4 µl/min. The gradient ran from 0 to 35% NH₄OAc in 40 minutes. For electrospray LC/MS/MS analysis, six fractions were collected and for MALDI LC/MS/MS 3 fractions were collected. The collected fractions were taken to dryness in a vacuum centrifuge.

ESI LC/MS/MS Analysis

The CEX derived fractions were reconstituted in 5 µl of 1% aqueous TFA, loaded onto the autosampler (FAMOS autosampler, LC Packings, Sunnyvale, Calif.) of the ESI LC/MS/MS system (LC packings Ultimate LC and either a Q Trap MS system, AB/MDS Sciex Toronto Canada, or an LCQ-Deca XP MS system, Thermo Finnigan, San Jose, Calif.), and injected onto a C-18 reverse phase trap cartridge (LC Packings) which was then washed for 1 minute at a flow rate of 50 µl/min using 0.5% aqueous acetic acid. The flow was then reversed and the peptides were back eluted onto a 75 micron×15 cm C-18 reverse phase LC column (LC Packings) for separation of the peptides at a flow rate of 250 nl/min. The loading buffer was 0.5% aqueous acetic acid and the elution buffer was AcN. MS data were collected in the information dependent mode in which one survey scan was acquired and then followed by the acquisition of three MS/MS spectra or two MS/MS spectra for the LCQ-Deca XP or Q Trap, respectively.

MALDI LC/MS/MS Analysis

MALDI MS/MS data were acquired in a two step process in which the CEX-derived fractions were reconstituted in 5 µl of 1% aqueous TFA and loaded onto the autosampler of an LC system (LC Packings) that spots the LC effluent directly onto a MALDI target while simultaneously mixing the effluent with MALDI matrix. Spots were deposited every 20 seconds and a total of 144 spots were collected for each CEX fraction. The samples were then analyzed by MALDI MS (AB 4700 Proteomics Analyzer, Applied Biosystems, Foster City, Calif.) to identify all of the usable peptide signals which were subsequently subjected to MS/MS analysis.

Example 15

Protein Identification by Database Searching

The proteins which were contained in the pull-down samples were identified by comparison of the MS/MS data to theoretical data derived from the human subset of the proteins contained in the NCBInr protein sequence database. The NCBInr protein sequence database was obtained by downloading it from the NCBI website. The matching of spectral data to the database was performed using a commercially available software package called Mascot which was purchased from Matrix Science (London, UK). The information from the separate CEX fractions derived from a single pull-down sample was combined before the database search to yield a single combined database search result from each pull-down.

The algorithm used by Mascot for protein identification uses a two step process in which MS/MS data is first assigned to multiple possible peptide ID's. The Mascot algorithm then assembles the putative peptide ID's into the minimum number of protein ID's that can explain the raw data. The output from Mascot was then further filtered based on the following criteria.

The protein level data had subtracted from it known false positives that were determined to be non-specific interactors on the basis of control experiments using the tag-only construct for pull-downs. Secondly, any proteins that were observed repeatedly across many pull-downs but not observed in the standard control experiment were also subtracted. Next, the proteins were ranked by the score assigned by Mascot and any proteins below a score of 60 were ignored.

The peptide level results from each listed protein were then screened to make sure that they met a minimum quality. All known interactors were considered identified if they had multiple peptides on which the identification was based or if there was only a single peptide, then its score alone was greater than or equal to 60.

In summary, the studies described in the above examples demonstrate that the present invention, i.e., a method of purifying a protein complex by using a modified bait protein containing affinity tags of high specificity separated by a specific protease cleavage site, can be used to purify protein complexes and their individual components comprising such complexes can be identified.

Table 3 below summarizes the results of the mass spectrometric analysis of the samples obtained by the method of the invention. Many proteins, that have been described in the literature as interacting with these three modified baits were identified with high confidence and are listed in column 3. A representative PubMed ID is given for a published paper for each identified interacting protein within which is described experimental evidence in support of these results. Column 5 indicates whether the interaction between the listed proteins and the baits is known to be direct (D), indirect (I) or undetermined (U). The observation of indirect partners of the exemplified bait proteins indicates that the present invention isolates complexes unapproachable by yeast two-hybrid and related methods.

TABLE 3

Summary of some of the interacting proteins identified using the invention.
Summary of known literature supported interactors identified by MS

| Bait | Vector | Interactors Found | GI Number | Direct, Indirect or Unknown | PubMed ID |
|---|---|---|---|---|---|
| Grb2 | E23 | Dynamin 2 | gi\|1706539 | D | 11746524 |
|  |  | dynamin internal form 1 long C-terminal form - human | gi\|539580 | D | 9452513 |
|  |  | GAP-associated tyrosine phosphoprotein p62 (Sam68) [Homo sapiens] | gi\|17512263 | D | 12112020 |
|  |  | JC7807 Wiskott-Aldrich syndrome protein (WASP)-interacting protein [Homo sapiens] | gi\|25528885 | D | 12007418 |
|  |  | WIRE protein [Homo sapiens] | gi\|18857714 | I | 12213210 |

TABLE 3-continued

Summary of some of the interacting proteins identified using the invention.
Summary of known literature supported interactors identified by MS

| Bait | Vector | Interactors Found | GI Number | Direct, Indirect or Unknown | PubMed ID |
|---|---|---|---|---|---|
| | | Wiskott-Aldrich syndrome gene-like protein; neural Wiskott-Aldrich syndrome protein [Homo sapiens] | gi|4505323 | D | 12147689 |
| Grb2 | E24 | Dynamin 2 | gi|1706539 | D | 11746524 |
| | | dynamin internal form 1 long C-terminal form - human | gi|539580 | D | 9452513 |
| | | GAP-associated tyrosine phosphoprotein p62 (Sam68) [Homo sapiens] | gi|17512263 | D | 12112020 |
| | E25 | Dynamin 2 | gi|1706539 | D | 11746524 |
| | | dynamin internal form 1 long C-terminal form - human | gi|539580 | D | 9452513 |
| | | GAP-associated tyrosine phosphoprotein p62 (Sam68) [Homo sapiens] | gi|17512263 | D | 12112020 |
| | | JC7807 Wiskott-Aldrich syndrome protein (WASP)-interacting protein [Homo sapiens] | gi|25528885 | D | 12007418 |
| | | WIRE protein [Homo sapiens] | gi|18857714 | I | 12213210 |
| | | Wiskott-Aldrich syndrome gene-like protein; neural Wiskott-Aldrich syndrome protein [Homo sapiens] | gi|4505323 | D | 12147689 |
| NAPA | E23 | syntaxin 6 | gi|2695737 | D | 8663448 |
| | | syntaxin 8 | gi|4433649 | U | 10683148 |
| | | syntaxin 18 | gi|8394376 | D | 10788491 |
| | | VAMP 4 | gi|3248920 | I | 10359608 |
| | | vesicle-associated membrane protein 8; endobrevin | gi|14043026 | I | 9614193 |
| | | SNAP-23 | gi|1374813 | U | 9647644 |
| | | synaptosomal-associated protein 29 kD [Homo sapiens] | gi|16307253 | U | 11444821 |
| | | vesicle-associated soluble NSF attachment protein receptor (v-SNARE) | gi|13111941 | U | 9705316 |
| | | N-ethylmaleimide-sensitive factor attachment protein gamma; soluble NSF attachment protein | gi|4505331 | U | 9705316 |
| | | vesicle transport-related protein | gi|12276129 | I | 11994317 |
| | | SEC22 vesicle trafficking protein (S. cerevisiae)-like 1 | gi|12655033 | U | 9166403 |
| | | is-Golgi SNARE p28 | gi|4234774 | D | 9325254 |
| | E24 | syntaxin 6 | gi|2695737 | D | 8663448 |
| | | syntaxin 8 | gi|4433649 | U | 10683148 |
| | | syntaxin 5 - human | gi|7513360 | D | 12435359 |
| | | Similar to syntaxin 12 | gi|28422538 | D | 9507000 |
| | | syntaxin 18 | gi|8394376 | D | 10788491 |
| | | VAMP 4 | gi|3248920 | I | 10359608 |
| | | vesicle-associated membrane protein 8; endobrevin | gi|14043026 | I | 9614193 |
| NAPA | E24 | SNAP-23 | gi|1374813 | U | 9647644 |
| | | synaptosomal-associated protein 29 kD [Homo sapiens] | gi|16307253 | U | 11444821 |
| | | vesicle-associated soluble NSF attachment protein receptor (v-SNARE) | gi|13111941 | U | 9705316 |
| | | N-ethylmaleimide-sensitive factor attachment protein gamma; soluble NSF attachment protein | gi|4505331 | U | 9705316 |
| | | vesicle transport-related protein | gi|12276129 | I | 11994317 |
| | | SEC22 vesicle trafficking protein (S. cerevisiae)-like 1 | gi|12655033 | U | 9166403 |
| | | cis-Golgi SNARE p28 | gi|4234774 | D | 9325254 |
| NAPA | E25 | syntaxin 6 | gi|2695737 | D | 8663448 |
| | | syntaxin 8 | gi|4433649 | U | 10683148 |
| | | syntaxin 5 - human | gi|7513360 | D | 12435359 |
| | | Similar to syntaxin 12 | gi|28422538 | D | 9507000 |
| | | vesicle-associated membrane protein 8 | gi|14043026 | I | 9614193 |
| | | SNAP-23 | gi|1374813 | U | 9647644 |
| | | synaptosomal-associated protein 29 kD | gi|16307253 | U | 11444821 |
| | | vesicle-associated soluble NSF attachment protein receptor (v-SNARE) | gi|13111941 | U | 9705316 |
| | | N-ethylmaleimide-sensitive factor attachment protein gamma; soluble NSF attachment protein | gi|4505331 | U | 9705316 |

TABLE 3-continued

Summary of some of the interacting proteins identified using the invention.
Summary of known literature supported interactors identified by MS

| Bait | Vector | Interactors Found | GI Number | Direct, Indirect or Unknown | PubMed ID |
|------|--------|-------------------|-----------|------------------------------|-----------|
|      |     | vesicle transport-related protein | gi|12276129 | I | 11994317 |
|      |     | SEC22 vesicle trafficking protein (*S. cerevisiae*)-like 1 | gi|12655033 | U | 9166403 |
|      |     | cis-Golgi SNARE p28 | gi|4234774 | D | 9325254 |
| CDKN1b | E23 | CDC2 polypeptide (CDC2) (AA 1-297) | gi|29839 | D | 12034920 |
|      |     | G2/mitotic-specific cyclin B1 | gi|116176 | D | 7478582 |
|      |     | cyclin A [*Homo sapiens*] | gi|510604 | D | 7478582 |
|      |     | cyclin dependent protein kinase (CDK4) | gi|1710234 | U | 9693368 |
|      | E24 | CDC2 polypeptide (CDC2) (AA 1-297) | gi|29839 | D | 12034920 |
|      |     | G2/mitotic-specific cyclin B1 | gi|116176 | D | 7478582 |
|      |     | cdk2 | gi|312803 | D | 9192873 |
|      |     | cyclin A [*Homo sapiens*] | gi|510604 | D | 7478582 |
|      |     | grb2 | gi|121603 | D | 11278754 |
|      |     | cdk3 | gi|4557439 | D | 9811456 |
|      |     | cdk5 | gi|13477283 | U | 12558068 |
|      |     | PCTAIRE protein kinase 1 | gi|15011928 | I | 12084709 |
|      |     | cyclin dependent protein kinase (CDK4) | gi|1710234 | U | 9693368 |
|      | E25 | CDC2 polypeptide (CDC2) (AA 1-297) | gi|29839 | D | 12034920 |
|      |     | G2/mitotic-specific cyclin B1 | gi|116176 | D | 7478582 |
|      |     | cdk2 | gi|312803 | D | 9192873 |
|      |     | cdk3 | gi|4557439 | D | 9811456 |
|      |     | cyclin dependent protein kinase (CDK4) | gi|1710234 | U | 9693368 |

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the invention is to be limited only to the claims except as precluded by the prior art. Moreover, the invention as disclosed herein, may be suitably practiced in the absence of the specific elements which are disclosed herein.

All references cited in the present application are incorporated in their entirety herein by reference to the extent not inconsistent herewith. Abbreviations and nomenclature, where employed, are deemed standard in the field and commonly used in professional journals such as those cited herein.

We claim:

1. A method for purifying a protein complex and individual components comprising the complex from a cell, a cell or tissue lysate, or an organism, comprising the steps carried out in the order set forth of:

a) providing a first binding component comprising four parts: 1) first affinity tag, 2) a protease specificity segment, 3) second affinity tag, and 4) a bait, wherein the first affinity tag has a greater affinity for its binding partner than the second affinity tag has for its binding partner, wherein the first affinity tag is biotinylated biotinylation recognition site, wherein said recognition sequence comprises the sequence set forth in SEQ ID NO:6, wherein the second affinity tag is proximal to the bait, and wherein said second affinity tag is His$_6$ hexapeptide, and wherein the protease specificity segment is located between said first affinity tag and said second affinity tag;

b) contacting the first binding component with a component of the protein complex, whereby part 4) of the first binding component binds to said component of the protein complex, thereby forming a bait-bound protein complex;

c) contacting the complex formed in step b) with a first affinity matrix specific for the first affinity tag thereby binding said complex to said matrix, and separating the complex from unbound material, and;

d) separating the individual components of the complex from the first binding component bound to the matrix, whereby the purified individual components are obtained.

2. The method of claim 1, wherein the method after step c) and in place of step d) further comprises, in the order set forth and in place of step d) of claim 1, the steps of:
   d) contacting the complex of step c) with a protease that specifically cleaves part 2) of the first binding component thereby cleaving the first binding component and forming a second binding component comprising parts 3) and 4) bound to the protein complex, but not bound to the first affinity matrix;
   e) contacting the second binding component with a second affinity matrix specific for the second affinity tag thereby binding the second binding component containing the protein complex to the second affinity matrix and separating the bait-bound protein complex from unbound material, and;
   f) separating the individual components of the complex from the second binding component bound to the second affinity matrix, whereby the purified individual components are obtained.

3. The method of claim 1, wherein the method after step c) further comprises, in the order set forth and in place of step d) of claim 1, the steps of:
   d) detaching the complex of step c) from the first affinity matrix;
   e) contacting the detached complex with a second affinity matrix specific for the second affinity tag thereby binding the complex to the second affinity matrix and further separating the bait-bound protein complex from unbound material, and;
   f) separating the individual components of the complex from the first binding component bound to the second affinity matrix, whereby the purified individual components are obtained.

4. The method of claim 1, wherein the method after step c) in place of step d) of claim 1, further comprises, in the order set forth, the steps of:
   d) detaching the bait-bound complex of step c) from the first affinity matrix under conditions where the individual components of the complex are partially dissociated from the complex under mildly denaturing conditions, and;
   e) contacting the detached complex and the dissociated individual components with a second affinity matrix specific for the second affinity tag thereby binding the first binding component to the second affinity matrix and separating the individual components from the first binding component, whereby the purified individual components are obtained.

5. The method of any of claims 1-4 wherein said protease specificity segment comprises an amino acid sequence cleavable by a protease selected from a group consisting of tobacco etch virus (TEV) protease, enterokinase, thrombin, a furin, and Factor Xa.

6. The method of claim 5 wherein said protease specificity segment comprises an amino acid sequence cleavable by TEV protease.

7. The method of claim 6 wherein said protease specificity segment comprises the sequence as shown in SEQ ID NO: 7.

8. The method of any of claims 1-4 wherein said bait comprises an amino acid sequence of a protein or a fragment thereof selected from the group consisting of cyclin D1, growth factor receptor-bound protein-2, proliferating cell nuclear antigen (PCNA), histone deacetylase 1(HDAC), cyclin-dependent kinase inhibitor 1b (CDKN1b), N-ethylmaleimide-sensitive factor attachment protein (NAPA), and cyclin-dependent kinase 5 (CDK5).

9. The method of any of claims 1-4, wherein after step (d) a purified individual component is identified by mass spectroscopy.

10. The method of claim 1, wherein the first affinity tag, a protease specificity segment and second affinity tag are incorporated within a polypeptide segment having the amino acid sequence set forth in SEQ ID NO:24.

11. The method of claim 1, wherein the first affinity tag, a protease specificity segment and second affinity tag are incorporated within a polypeptide segment having the amino acid sequence set forth in SEQ ID NO:22.

12. The method of claim 1 wherein the protein complex in step (b) is prepared by lysis of cells comprising the protein complex in a buffer comprising 1 mM dithiothreitol.

13. The method of claim 1 wherein the protein complex in step (b) is prepared by centrifuging a cell lysate comprising said complex at 27,000×g.

14. The method of claim 12 wherein the protein complex is prepared by centrifuging a cell lysate comprising the protein complex at 27,000×g.

* * * * *